United States Patent [19]

Clader et al.

[11] Patent Number: 5,416,118
[45] Date of Patent: May 16, 1995

[54] BICYCLIC AMIDES AS INHIBITORS OF ACYL-COENZYME A: CHOLESTEROL ACYL TRANSFERASE

[75] Inventors: John W. Clader, Cranford, N.J.; Thomas Fevig, West Chester, Ohio; Wayne Vaccaro, Yardley, Pa.; Joel G. Berger, Cedar Grove, N.J.

[73] Assignee: Schering Corporation, Kenilworth, N.J.

[21] Appl. No.: 122,537

[22] PCT Filed: Apr. 9, 1992

[86] PCT No.: PCT/US92/02662

§ 371 Date: Sep. 28, 1993

§ 102(e) Date: Sep. 28, 1993

[87] PCT Pub. No.: WO92/18462

PCT Pub. Date: Oct. 29, 1992

[51] Int. Cl.⁶ .............. C07C 233/11; A61K 31/165; A61K 31/44; A61K 31/35

[52] U.S. Cl. .............. 514/617; 514/357; 514/456; 514/596; 514/619; 514/621; 514/622; 514/625; 514/627; 514/630; 546/337; 549/399; 549/400; 549/404; 564/55; 564/163; 564/165; 564/166; 564/167; 564/168; 564/170; 564/174; 564/177; 564/179; 564/181; 564/182; 564/200; 564/202; 564/207; 564/218

[58] Field of Search .............. 514/617, 619, 622, 824, 514/357, 596, 621, 625, 627, 630; 564/163, 165, 166, 168, 35, 167, 169, 170, 174, 177, 179, 181, 182, 200, 202, 207, 218; 546/337

[56] References Cited

U.S. PATENT DOCUMENTS

| | | | |
|---|---|---|---|
| 3,704,323 | 11/1972 | Krapcho | 260/576 |
| 4,248,893 | 2/1981 | Kathawala et al. | 424/324 |
| 4,456,619 | 6/1984 | Kathawala | 424/324 |
| 4,888,355 | 12/1989 | Clemence et al. | 514/429 |
| 5,071,875 | 12/1991 | Horn et al. | 514/613 |

FOREIGN PATENT DOCUMENTS

| | | | |
|---|---|---|---|
| 173331 | 3/1986 | European Pat. Off. | C07C 91/28 |
| 250077 | 12/1987 | European Pat. Off. | C07D 405/09 |
| 6509640 | 1/1966 | Netherlands | |

OTHER PUBLICATIONS

Derwent Abstract 50885B/28: BE 873,365 (1979).
Chemical Abstracts 59: 611c (1962), Takahashi et al.
Chemical Abstracts 64: 19517b (1966), Olin Mathieson.
Gopinath et al, J. Chem. Soc., (1957), pp. 4760–4765.
Broquet et al, Comptes Rendus, 258, 6 (1964), pp. 1820–1823.
Kametani et al, Chem. Pharm. Bull., 19, 6 (1971), pp. 1150–1157.
Yamaguchi, et al, Bull. Chem. Soc. Japan, 41, 9 (1968), pp. 2073–2077.
Ishii et al, Chem. Pharm. Bull., 31, 9 (1983), pp. 3056–3073.

Primary Examiner—Peter O'Sullivan
Attorney, Agent, or Firm—Anita W. Magatti; Eric S. Dicker

[57] ABSTRACT

Novel bicyclic amides of the formula

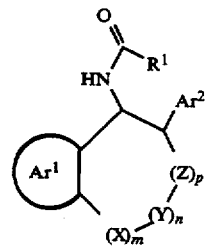

wherein $Ar^1$ and $Ar^2$ are phenyl, $R^2$-substituted phenyl, heteroaryl or $R^2$-substituted heteroaryl, wherein $R^2$ is 1 to 3 substituents independently selected from the group consisting of halogeno, hydroxy, lower alkyl, lower alkoxy, nitro, amino, lower alkylamino and lower dialkylamino;

X, Y and Z are $-CH_2-$, $-CH(alkyl)-$, $-C(alkyl)_2-$, $-NH-$, $-N(alkyl)-$, $-O-$ or $-SO_r$, wherein r is 0, 1 or 2, and m, n and p are 0 or 1;

$R^1$ is an alkyl chain of 1 to 25 carbon atoms; an alkyl chain substituted by one or more optionally substituted phenyl or heteroaryl groups; an alkyl chain (Abstract continued on next page.)

—O—, —SO$_n$, phenylene, R$^2$-substituted phenylene, heteroarylene or R$^2$-substituted heteroarylene groups; an interrupted alkyl chain substituted by one or more optionally substituted phenyl or heteroaryl groups; an alkyl chain of 4 to 25 carbon atoms, interrupted by one or more —NH—, —C(O)— or —N(lower alkyl)— groups; an interrupted alkyl chain of 4 to 25 carbon atoms substituted by one or more phenyl, R$^2$-substituted phenyl, heteroaryl or R$^2$-substituted heteroaryl groups; a diphenylamino group; a di-(R$^2$-substituted phenyl)amino group; a diheteroarylamino group; or a di-(R$^2$-substituted heteroaryl)amino group;

or a pharmaceutically acceptable salt thereof, useful in the treatment of artherosclerosis are disclosed.

12 Claims, No Drawings

BICYCLIC AMIDES AS INHIBITORS OF ACYL-COENZYME A: CHOLESTEROL ACYL TRANSFERASE

BACKGROUND OF THE INVENTION

The present invention relates to bicyclic amides and to pharmaceutical compositions containing such compounds, for use in the treatment and prevention of atherosclerosis.

Atherosclerotic coronary heart disease represents the major cause for death and cardiovascular morbidity in the western world. Risk factors for atherosclerotic coronary heart disease include hypertension, diabetes mellitus, family history, male sex, cigarette smoking and serum cholesterol. A total cholesterol level in excess of 225–250 mg/dl is associated with significant elevation of risk.

Cholesterol esters are a major component of atherosclerotic lesions and the major storage form of cholesterol in arterial wall cells. Formation of cholesterol esters is also a key step in the intestinal absorption of dietary cholesterol. The intracellular esterification of cholesterol is catalyzed by the enzyme acyl CoA:-cholesterol acyl transferase (ACAT, EC 2.3.1.26). Thus, inhibition of ACAT is likely to inhibit the progression of atherosclerotic lesion formation, decrease the accumulation of cholesterol esters in the arterial wall, and block the intestinal absorption of dietary cholesterol.

A number of bicyclic amides have been reported as being useful in lowering cholesterol and/or inhibiting formation of cholesterol-containing lesions in mammalian arterial walls. U.S. Pat. No. 4,456,619 to Kathawala discloses compounds of the formula

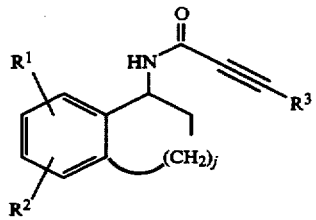

wherein $R^1$ and $R^2$ are independently H, lower alkyl, lower alkoxy or halo; j is an integer of from 1 to 3; and $R^3$ is an alkyl chain of 1 to 23 carbon atoms, saturated or unsaturated, or an alkyl chain as defined wherein each unsaturated ethylenic group is replaced by a cyclopropanyl group.

U.S. Pat. No. 4,248,893 to Kathawala et al discloses compounds of formula

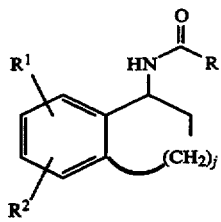

wherein j is an integer of from 1 to 3; $R^1$ and $R^2$ are independently H, halo, lower alkyl or lower alkoxy; and —C(O)—R is a 7–23 C unsaturated fatty acid radical in which each ethylenic group is replaced by a cyclopropanyl group.

While some of these bicyclic amides have shown in vitro ACAT inhibitory activity, none have been reported to show significant activity in whole animal models of atherosclerosis.

In addition, U.S. Pat. No. 3,704,323 to Krapcho discloses CNS stimulant 2-methyl-2-phenylindanamines of the formula

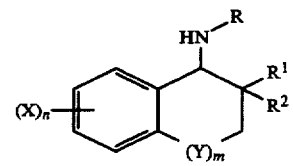

wherein X is H, OH, lower alkyl, halogen, lower alkoxy, amino or dialkylamino; Y is —CH$_2$—, —CH$_2$CH$_2$—, —O— or —S—; n is 1, 2 or 3; m is 0 or 1; $R^1$ is phenyl, pyridyl, or X-substituted phenyl or pyridyl; $R^2$ is lower alkyl or X-substituted aryl; and R is lower alkyl or hydroxy- or phenyl-substituted lower alkyl.

European Patent Application 250,077 to Evans et al discloses hypotensive compounds of the formula

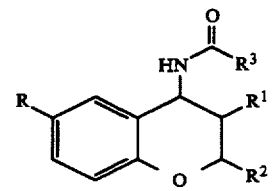

wherein R is alkyl; $R^1$ is alkoxy or acyloxy; $R^2$ is lower alkyl; and $R^3$ is lower alkyl, aryl or heteroaryl.

SUMMARY OF THE INVENTION

Novel compounds of the present invention which show significant in vivo anti-atherosclerotic activity are represented by the formula

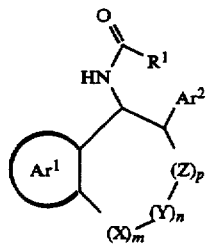

I wherein $Ar^1$ and $Ar^2$ are independently selected from the group consisting of phenyl, $R^2$-substituted phenyl, heteroaryl or $R^2$-substituted heteroaryl, wherein $R^2$ is 1 to 3 substituents independently selected from the group consisting of halogeno, hydroxy, lower alkyl, lower alkoxy, nitro, amino, lower alkylamino and lower dialkylamino;

X, Y and Z are independently selected from the group consisting of —CH$_2$—, —CH(alkyl)—, —C(alkyl)$_2$—, —NH—, —N(alkyl)—, —O— and —SO$_r$, wherein r is 0, 1 or 2, and m, n and p are 0 or 1, such that 0<(m+n+p)<4, provided that only one of X,Y or Z is —NH—, —N(alkyl)—, —O— or —SO$_r$;

$R^1$ is an alkyl chain of 1 to 25 carbon atoms, branched or straight, saturated or containing one or more double bonds; an alkyl chain of 1 to 25 carbon atoms as defined substituted by one or more substituents selected from the group consisting of phenyl, $R^2$-substituted phenyl, heteroaryl and $R^2$-substituted heteroaryl; an alkyl chain of 1 to 25 carbon atoms as defined interrupted by one or more Q groups, wherein Q is independently selected from the group consisting of —O—, —$SO_n$, phenylene, $R^2$-substituted phenylene, heteroarylene and $R^2$-substituted heteroarylene; an interrupted alkyl chain of 1 to 25 carbon atoms as defined substituted by one or more substituents selected from the group consisting of phenyl, $R^2$-substituted phenyl, heteroaryl and $R^2$-substituted heteroaryl; an alkyl chain of 4 to 25 carbon atoms, interrupted by one or more groups selected from the group consisting of Q, —NH—, —C(O)— and —N(lower alkyl)—; an interrupted alkyl chain of 4 to 25 carbon atoms as defined substituted by one or more substituents selected from the group consisting of phenyl, $R^2$-substituted phenyl, heteroaryl and $R^2$-substituted heteroaryl; a diphenylamino group; a di-($R^2$-substituted phenyl)amino group; a diheteroarylamino group; or a di-($R^2$-substituted heteroaryl)amino group; or a pharmaceutically acceptable salt thereof.

Preferred are compounds of formula I wherein —(X)$_m$—(Y)$_n$—(Z)$_p$—, together with the carbons to which they are attached, form a 6-C ring; $Ar^1$ and $Ar^2$ are independently selected from the group consisting of phenyl, lower alkoxy-substituted phenyl, amino-substituted phenyl, hydroxy-substituted phenyl or pyridyl.

Another group of preferred compounds is that wherein one of X, Y or Z is an oxygen atom and —(X)$_m$—(Y)$_n$—(Z)$_p$—, together with the carbons to which they are attached, form a six membered ring containing one oxygen atom, and $Ar^1$ and $Ar^2$ are both phenyl.

Also preferred are compounds wherein —(X)$_m$—(Y)$_n$—(Z)$_p$—, together with the carbons to which they are attached, form a 7-C ring, and $Ar^1$ and $Ar^2$ are independently selected from the group consisting of lower alkoxy-substituted phenyl or hydroxy-substituted phenyl.

Yet another group of preferred compounds is that wherein —(X)$_m$—(Y)$_n$—(Z)$_p$—, together with the carbon to which they are attached, form a 5-C ring, and $Ar^1$ and $Ar^2$ are independently chosen from the group consisting of phenyl, nitro-substituted phenyl, amino-substituted phenyl, lower alkoxy-substituted phenyl and hydroxy-substituted phenyl.

Still another group of preferred compounds is that wherein $R^1$ is 1,1-dimethyldecanyl (i.e. —C(O)$R^1$ is 2,2-dimethylundecanoyl); $CH_3(CH_2)_7CH=CH(CH_2)_7$—(i.e. —C(O)$R^1$ is oleoyl); diphenylamino; or a diphenyl substituted alkyl chain, especially diphenylmethyl (i.e. —C(O)$R^1$ is diphenylacetyl).

Especially preferred are compounds of formula I wherein —(X)$_m$—(Y)$_n$—(Z)$_p$—, together with the carbons to which they are attached, form a 5-C ring; $Ar^1$ is phenyl; $Ar^2$ is hydroxy-substituted phenyl and $R^1$ is diphenylmethyl.

This invention also relates to the use of the ACAT inhibitors of the present invention as hypolipidemic and hypocholesterolemic agents in mammals.

In another aspect, the invention relates to pharmaceutical compositions comprising an ACAT inhibitor of the present invention in a pharmaceutically acceptable carrier.

DETAILED DESCRIPTION

Generally accepted abbreviations are used throughout the specification and claims to identify solvents and reagents as follows: N,N-dimethylformamide (DMF); 1-hydroxy-benzotdazole (HOBT); tetrahydrofuran (THF); dicyclohexylcarbodiimide (DCC); 1-(3'-dimethylaminopropyl)-3-ethylcarbodiimide hydrochloride (EDCI); methanol (MeOH); ethyl acetate (EtOAc); diisobutylaluminum hydride (DIBAL-H); N-bromosuccinimide (NBS); palladium on carbon (Pd/C); triethylamine ($Et_3N$); N,N-dimethylaminopyridine (DMAP); N-methylmorpholine (NMM); p-toluenesulfonic acid (pTSA); hydrochloric acid (HCl); triphenylphosphine ($Ph_3P$); diethylazodicarboxylate (DEAD); ethanol (EtOH); ethanethiol (EtSH); sodium acetate (NaOAc); glacial acetic acid (HOAc); diethyl ether (ether).

As used herein, the term "lower alkyl" means straight or branched alkyl chains of 1 to 6 carbon atoms and "lower alkoxy" similarly refers to alkoxy groups having 1 to 6 carbon atoms.

Halogeno refers to fluorine, chlorine, bromine or iodine radicals.

"Phenylene" means a bivalent phenyl group, including ortho, meta and para-substitution and "heteroarylene" similarly means a bivalent heteroaryl group.

Heteroaryl means an aromatic group having 5 or 6 ring members wherein 1-3 ring members are independently selected from the group consisting of nitrogen, oxygen and sulfur. Examples of heteroaryl groups are pyridyl, pyrimidinyl, pyrazinyl, triazinyl, pyrrolyl, furanyl and thienyl.

The alkyl chain as defined in $R^1$ can be a radical of a synthetic or natural fatty acid, either saturated or containing one or more carbon to carbon double bonds, or can be an interrupted alkyl chain wherein one or more of the carbon atoms in the chain can be replaced by an —O—, —$SO_n$, phenylene or heteroarylene group; and when the alkyl chain is greater than 4 carbons in length it can be additionally interrupted by —NH—, —N(lower alkyl)—, or —C(O)— group. When substituted by optionally substituted phenyl or heteroaryl groups, the alkyl chain or interrupted alkyl chain may be independently substituted on different carbon atoms, di-substituted on one carbon atom, or both.

One skilled in the art will recognize that the number of double bonds present, the replacement of carbon atoms in the chain and the presence of substituents on the carbon atoms in the chain are all dependent on the length of the chain: shorter alkyl chains cannot accommodate as many bonds, carbon replacements or substituents as longer alkyl chains. In general, unsaturated alkyl chains contain 1 to 4 double bonds, conjugated or non-conjugated. Where carbon atoms are replaced, 1 to 4 replacement groups can be present. Similarly, when carbon atoms in the chain are substituted, 1 to 4 substituents can be present.

Examples of alkyl chains are as follows, wherein the group —C(O)$R^1$ is named: palmitoyl, stearoyl and 2,2-dimethyldodecanoyl.

Examples of unsaturated —C(O)$R^1$ groups are oleoyl, linoleoyl, linolenoyl, elaidoyl, eicosatetraenoyl, eicosapentaenoyl and arachidonoyl.

Examples of —C(O)$R^1$ groups wherein the carbon atoms are substituted are diphenylacetyl, 3,3-diphenylpropionyl and 2,3-diphenylpropionyl.

Examples of —C(O)$R^1$ groups wherein carbon atoms in the chain are replaced are: 3-methoxy-4-(tetradecyloxy)-benzoyl, 11-[N-(2,2-diphenylacetyl-)amino]undecanoyl and phenoxyundecanoyl.

An example of a di-substituted amino —C(O)R$^1$ group is N,N-diphenylaminocarbonyl.

Compounds of the invention have at least two asymmetrical carbon atoms and therefore include rotational isomers. The invention includes all possible stereoisomers in both pure form and in admixture, including racemic mixtures. Isomers can be prepared using conventional techniques, either by reacting enantiomeric starting materials or by separating isomers of a compound of formula I.

Isomers may include geometric isomers, e.g. when R$^1$ contains a double bond. All such isomers are contemplated for this invention.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a phenol or carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formula I can be prepared under standard reaction conditions well known in the art. For example, a carboxylic acid of formula II can be converted to the acid chloride by treatment with thionyl or oxalyl chloride in a solvent such as CH$_2$Cl$_2$, then reacted with an amine of formula III in the presence of a tertiary amine base such as Et$_3$N, DMAP or NMM:

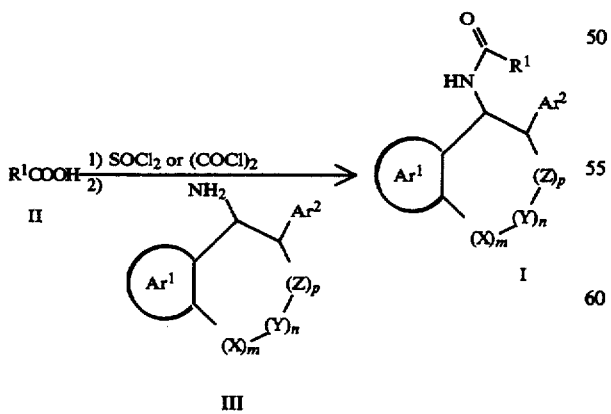

Alternatively, the acid of formula II and the amine of formula III can be reacted in the presence of a coupling agent such as DCC or EDCI and a base such as Et$_3$N, DMAP or NMM in a solvent such as CH$_2$Cl$_2$ or THF at a temperature of 0° C. to 23° C. In a third method, the carboxy group of acid II can be activated via the intermediacy of an active ester such as that derived from HOBT.

Starting compounds of formula II are commercially available or can be prepared by well known methods.

Compounds of formula Ib, wherein one of Ar$^1$ or Ar$^2$ is R$^2$-substituted phenyl and R$^2$ is hydroxy, can be prepared by treating a compound of formula Ia, wherein one of Ar$^1$ or Ar$^2$ is R$^2$-substituted phenyl and R$^2$ is methoxy, with BBr$_3$. In an alternative method, a compound of formula Ia can be added to a mixture of NaH and EtSH in DMF and heated at reflux to prepare a compound of formula Ib.

Compounds of formula Id, wherein one of Ar$^1$ or Ar$^2$ is R$^2$-substituted phenyl and R$^2$ is a primary amino group, can be prepared by hydrogenation over a suitable catalyst, e.g. 5% Pd/C, of a compound of formula Ic, wherein one of Ar$^1$ or Ar$^2$ is R$^2$-substituted phenyl and R$^2$ is a nitro group.

Compounds of formula If, wherein R$^1$ is N,N-diphenylamino, can be prepared by treatment of an amine of formula III with triphosgene and Et$_3$N followed by reaction with diphenylamine at reflux:

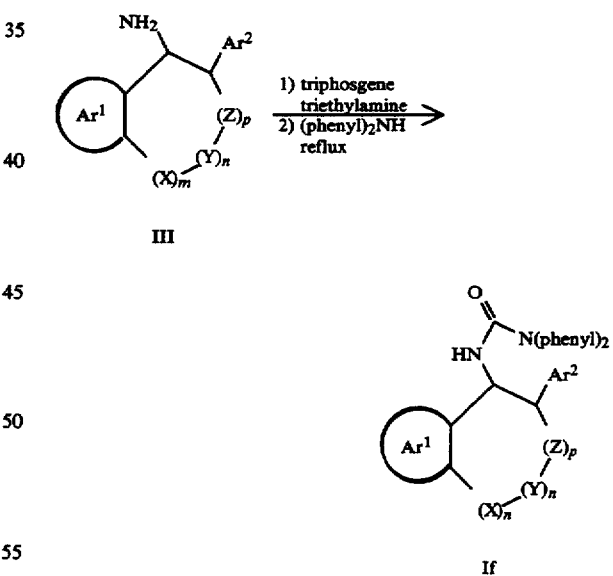

Compounds of the formula Ig, wherein R$^{2a}$ and R$^{2b}$ are independently hydrogen, bromo, chloro or methyl, can be prepared from a compound of formula Ih, i.e., a compound of formula I wherein Ar$^2$ is 4-hydroxyphenyl, by a variety of methods. In a method for preparing compounds of the formula Ig, wherein one of R$^{2a}$ or R$^{2b}$ is bromo and the other is hydrogen, a compound of the formula Ih is treated with a suitable brominating agent, e.g. NBS, in dry DMF.

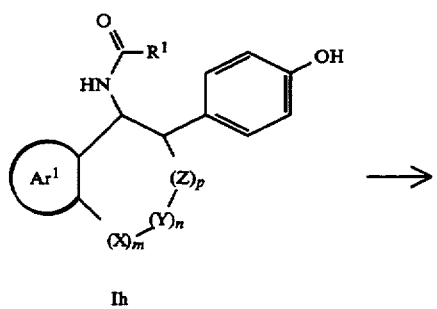

Ih

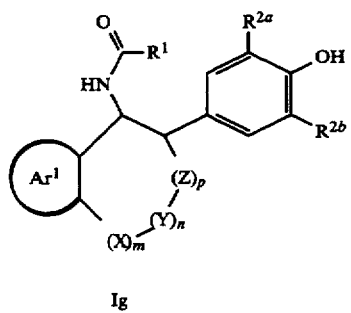

Ig

Compounds of the formula Ig, wherein $R^{2a}$ and $R^{2b}$ are independently hydrogen or chloro, can be prepared by treating a compound of the formula Ih with an appropriate quantity of a suitable chlorinating agent, e.g. sulfuryl chloride, in dry organic solvent, e.g. a mixture of $CH_2Cl_2$ and ether.

A method for preparing a compound of the formula Ig, wherein $R^{2a}$ and $R^{2b}$ are independently hydrogen or methyl comprises treating a compound of the formula Ih with formaldehyde, 10% aqueous KOH in DMF and heating the mixture followed by hydrogenation of the product so obtained at elevated pressure, e.g. 60 psi hydrogen, with a suitable catalyst, e.g. 20% $Pd(OH)_2$ on carbon, and using an appropriate solvent, e.g. HOAc.

Amines of formula III can be prepared by several methods. In one method, a ketone of formula IV is reacted with methoxyamine hydrochloride and NaOAc in a solvent such as MeOH to obtain an oxime methyl ether of formula V. The oxime ether is reduced to the desired amine III (as a mixture of cis and trans isomers), by treatment with a suitable reducing agent such as borane or alternatively by reduction with hydrogen gas at 50 psi in the presence of a suitable catalyst such as 10% Pd/C:

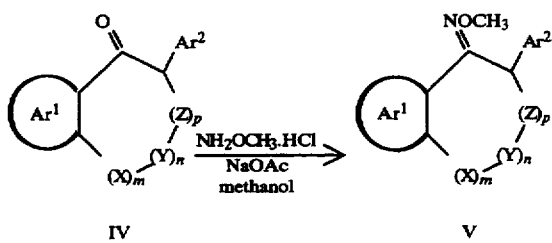

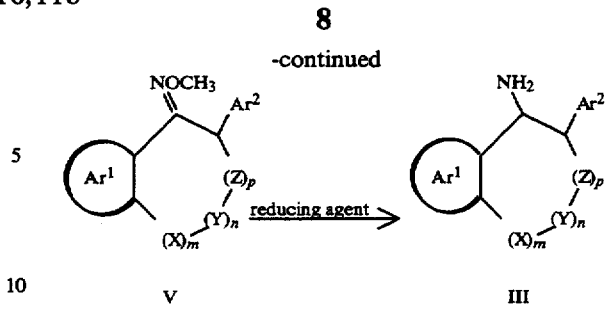

In a method of preparing a cis-amine of formula III-cis, a ketone of formula IV is converted to an oxime of formula XXV by treatment with hydroxylamine hydrochloride and NaOAc in MeOH. The oxime XXV is treated with chlorodiphenylphosphine and $Et_3N$ to form a phosphinylimine XXVI. Reduction of the phosphinylimine to a cis-phosphonamide XXVII with DIBAL-H followed by hydrolysis with HCl in MeOH forms the desired cis-amine:

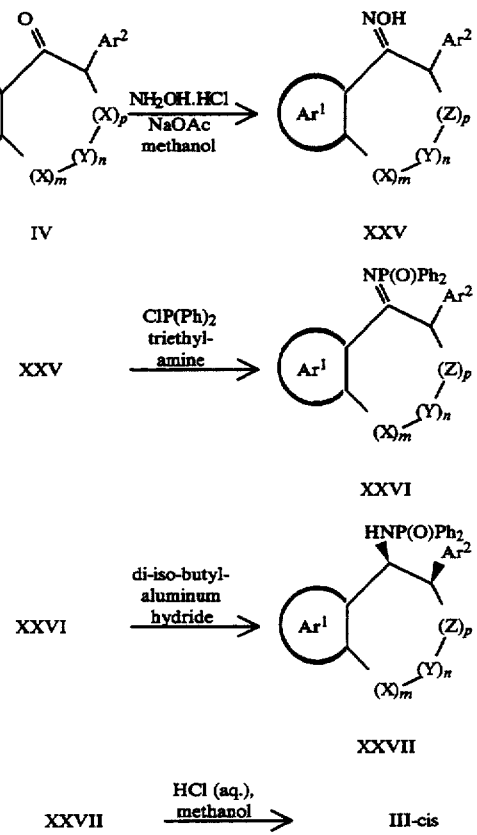

A second method of preparing a cis-amine of formula III-cis involves reducing a ketone of formula IV with $NaBH_4$. The resulting alcohol VI is dehydrated by treating with pTSA in refluxing toluene to form an olefin XXVIII. The olefin is reacted with borane-THF complex then oxidized with $H_2O_2$ and base to produce the trans-alcohol VI-trans. The trans-alcohol is converted to the corresponding cis-azide VII-cis by reaction with diphenylphosphoryl azide, DEAD and $Ph_3P$. Reduction of the azide to the desired amine III-cis is accomplished by reaction with hydrogen gas at 50–60 psi in the presence of a suitable catalyst such as 10% Pd/C:

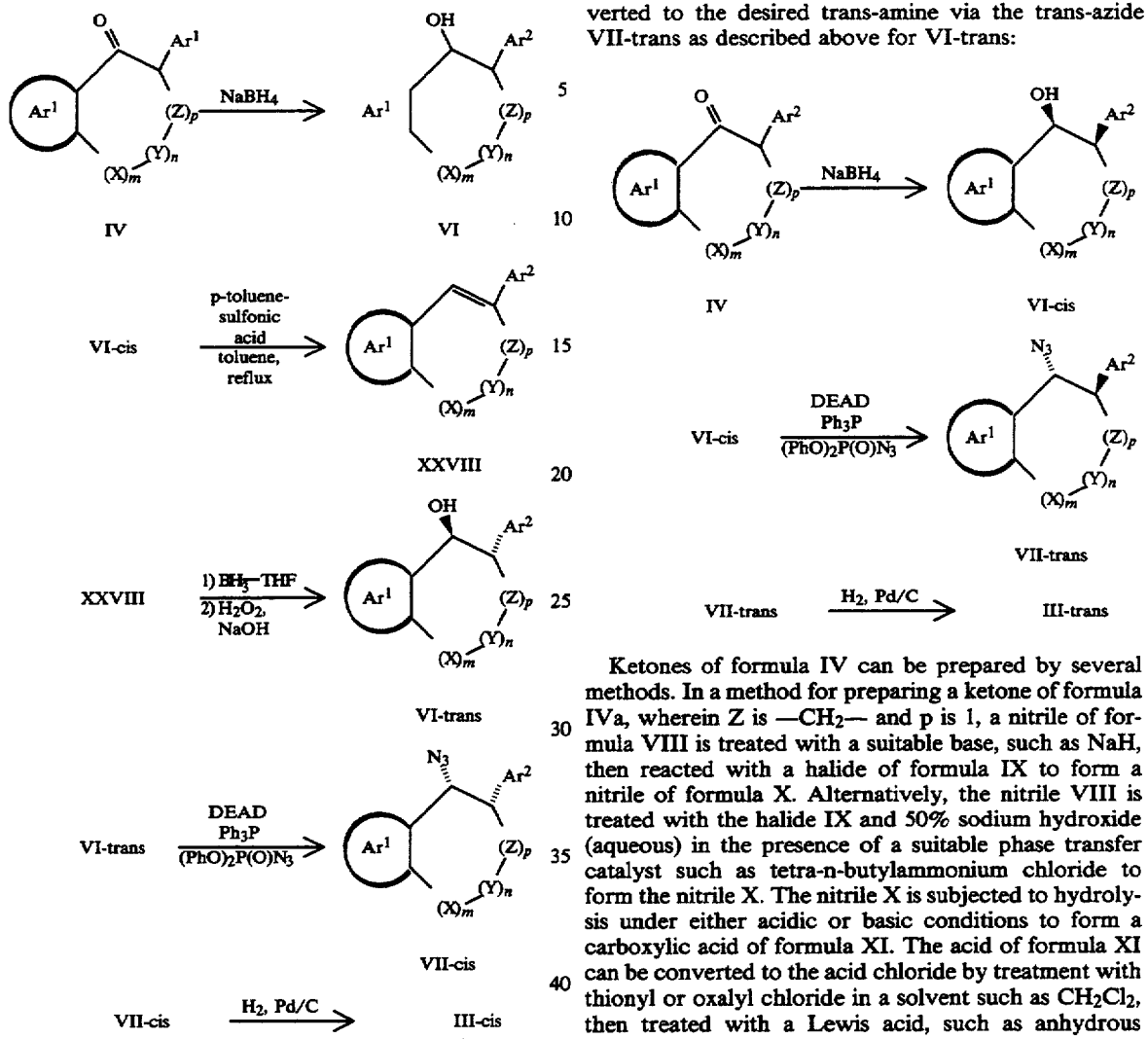

A method for preparing a trans-amine of formula III-trans involves reducing a ketone of formula IV to a cis-alcohol of formula VI-cis using a suitable reducing agent, such as DIBAL-H. The alcohol VI-cis is converted to the desired trans-amine via the trans-azide VII-trans as described above for VI-trans:

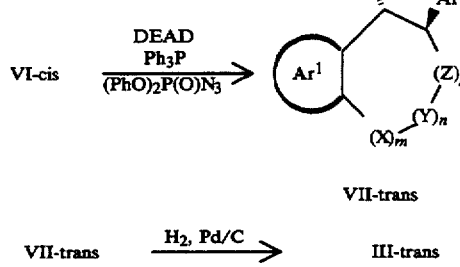

Ketones of formula IV can be prepared by several methods. In a method for preparing a ketone of formula IVa, wherein Z is —CH$_2$— and p is 1, a nitrile of formula VIII is treated with a suitable base, such as NaH, then reacted with a halide of formula IX to form a nitrile of formula X. Alternatively, the nitrile VIII is treated with the halide IX and 50% sodium hydroxide (aqueous) in the presence of a suitable phase transfer catalyst such as tetra-n-butylammonium chloride to form the nitrile X. The nitrile X is subjected to hydrolysis under either acidic or basic conditions to form a carboxylic acid of formula XI. The acid of formula XI can be converted to the acid chloride by treatment with thionyl or oxalyl chloride in a solvent such as CH$_2$Cl$_2$, then treated with a Lewis acid, such as anhydrous AlCl$_3$, to form the ketone IVa:

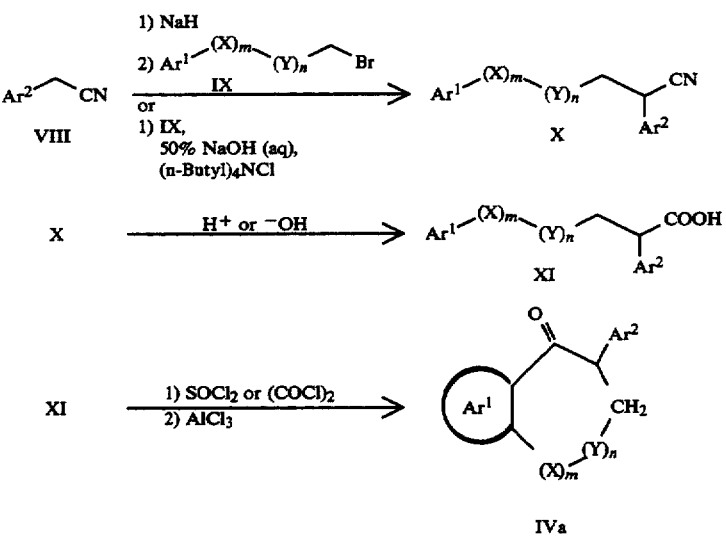

Alternatively, a nitrile of formula X can be combined with NaCl and AlCl₃, then heated to 180° C., followed by hydrolysis to directly form the ketone IVa.

Starting nitriles of formula VIII and halides of formula IX are commercially available or can be prepared by well known methods.

In a second method of preparing ketones of formula IVa, a nitrile of formula VIII is condensed with an aldehyde of formula XXI under basic conditions to form an unsaturated nitrile of formula XXII. The unsaturated nitrile of formula XXII is reduced using NaBH₄ in EtOH to a nitrile of formula X which is converted to a ketone of formula IVa as described above:

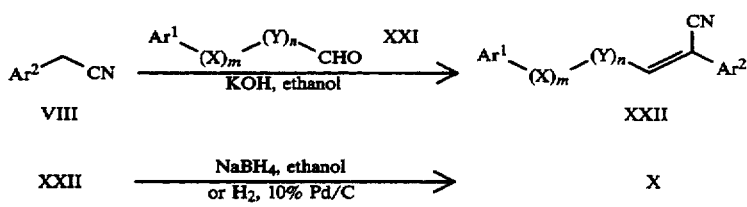

Alternatively, the unsaturated nitrile XXII can be reduced by hydrogenation at 50 psi of hydrogen in the presence of a suitable catalyst such as 10% Pd/C.

Starting aldehydes of formula XXI and nitriles of formula VIII are commercially available or can be prepared by methods well known to those skilled in the art.

In a method of preparing a ketone of formula IVb, wherein R³ is H or alkyl and —(X)$_m$—(Y)$_n$—(Z)$_p$—, together with the carbons to which they are attached, comprise a 6-C ring, a ketone of formula XII is condensed with an aldehyde of formula XIII under basic conditions to form a ketone of the formula XIV. The ketone of formula XIV is reacted with potassium cyanide and HOAc to form a ketonitrile of formula XV. Hydrolysis of the nitrile XV gives the keto-acid XXIX which is reduced with hydrogen gas at 50 psi in the presence of a suitable catalyst such as 10% Pd/C to a carboxylic acid of formula XXX. The acid of formula XXX can be converted to a ketone of the formula IVb via the process described above for XI:

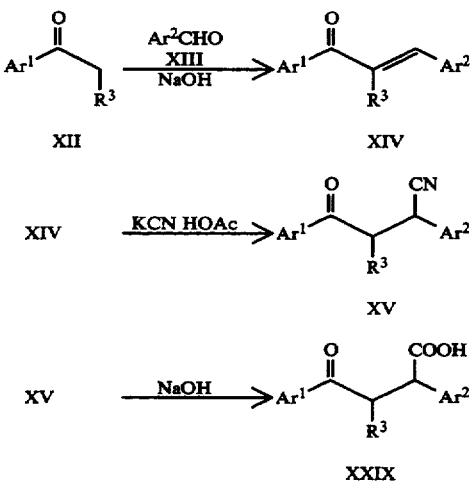

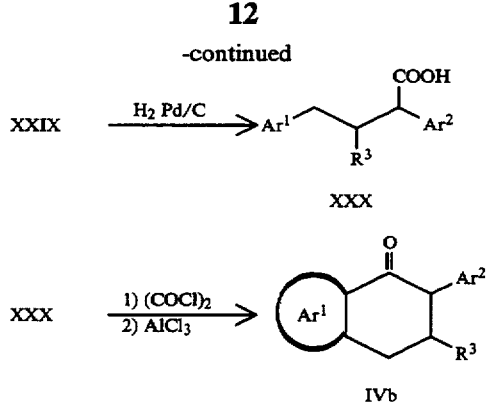

Starting ketones of formula XII and aldehydes of formula XIII are commercially available or can be prepared by well known methods.

A ketone of formula IV can be prepared by treatment of a ketone of formula XVI with chlorine to form an α-chloro-ketone of formula XVII. Treatment of the chloroketone XVII with an organometallic reagent of formula XVIII, wherein M is Li, Ce or MgBr produces an alcohol of formula XIX. Reaction of the alcohol XIX with ethylgrignard reagent in a suitable solvent such as THF at reflux temperature forms the desired ketone IV:

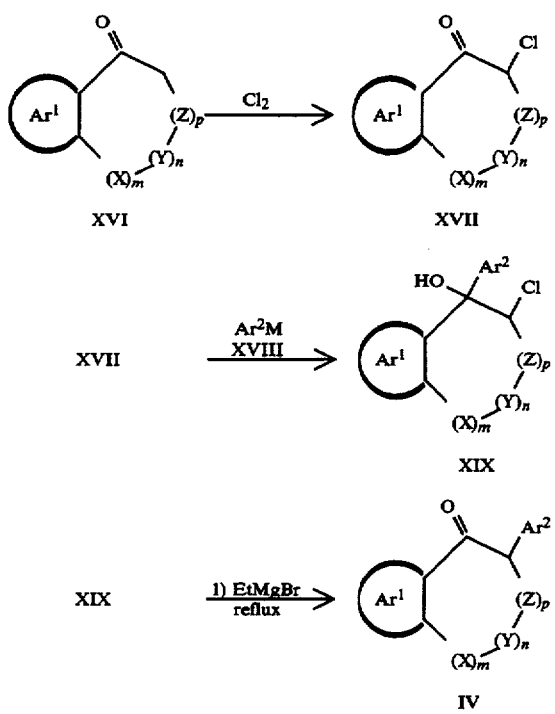

Starting ketones of formula XVI and organometallic reagents of formula XVIII are commercially available or can readily be prepared via procedures well known to those skilled in the art.

Another method of preparing a ketone of formula IV involves reacting an enol acetate of formula XX with an aryl halide of formula XXI and tri-n-butyltin methoxide in the presence of a suitable catalyst such as [(ortho-tolyl)$_3$P]$_2$PdCl$_2$:

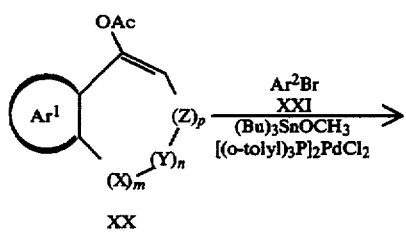

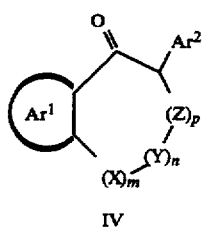

In a method for preparing ketones of formula IVc, wherein Ar$^1$ is R$^2$-substituted phenyl; and —(X)$_m$—(Y)$_n$—(Z)$_p$—, together with the carbons to which they are attached, comprise a 5-C ring, an aldehyde of formula XIII and a lactone of formula XXIII are treated with sodium ethoxide in EtOH at reflux to form an indanedione of formula XXIV. The indanedione of formula XXIV is treated with NH$_4$OAc in EtOH at reflux, then reduced with zinc dust to form the desired ketone IVc:

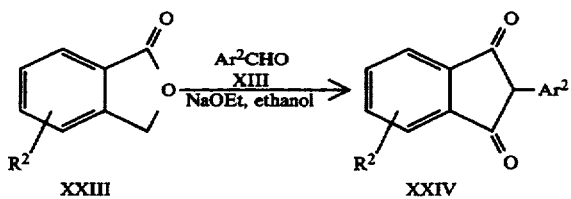

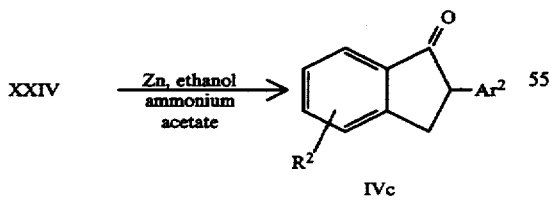

Starting lactones of formula XXIII and aldehydes of formula XIII are commercially available or can be prepared by methods well known to those skilled in the art.

Enol acetates of formula XX can be prepared by reacting a ketone of formula XVI with isopropenyl acetate in the presence of a catalytic amount of a suitable acid, such as pTSA.

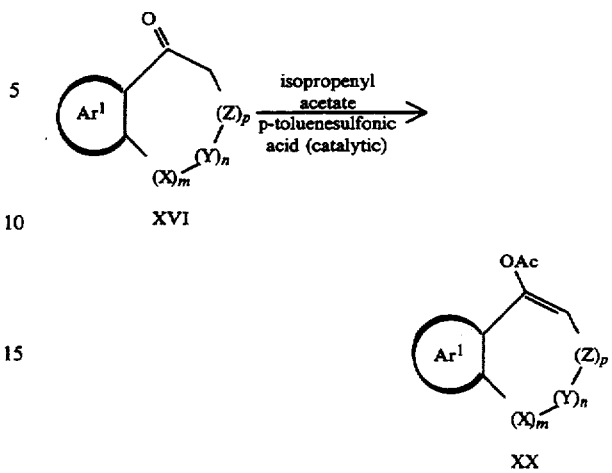

Starting ketones of formula XVI are commercially available or readily prepared by well known methods.

Reactive groups not involved in the above processes can be protected during the reactions with conventional protecting groups which can be removed by standard procedures after the reaction. The following table shows some typical protecting groups:

| Group to be protected | Protected group |
| --- | --- |
| —OH | —OCH$_3$ |
| —NH$_2$ |  |
| —COOH | —COOalkyl, —COObenzyl, —COOphenyl |

We have found that the compounds of this invention are inhibitors of ACAT in vitro and in whole animal models the compounds have been found to significantly reduce the formation of liver cholesterol esters. Thus, compounds of this invention are hypocholesterolemic and hypolipidemic agents by virtue of their ability to inhibit the esterification and intestinal absorption of cholesterol; they are therefore useful in the treatment and prevention of atherosclerosis in mammals, in particular in humans.

In addition to the compound aspect, the present invention therefore also relates to a method of treating atherosclerosis, in particular by reducing serum cholesterol, which method comprises administering to a mammal in need of such treatment a hypocholesterolemic effective amount of a compound of this invention. The compound is preferably administered in a pharmaceutically acceptable carrier suitable for oral administration.

The in vitro and in vivo activity of the present compounds can be determined by the following procedures.

ACAT Assay (in vitro)

This assay measures the activity of ACAT by measuring the ACAT-mediated transfer of tritiated oleic acid from acyl-CoA to cholesterol to give labelled cholesterol oleate. Rat liver microsomes are used as the source of ACAT. Assays are performed in round bottom microtiterplates using a total incubation volume of 50 μL.

Each incubation well receives 10 μL assay buffer (0.5M KHPO$_4$, 10 μM dithiothreitol, pH 7.4), 7.5 μL of 40 mg/mL BSA (Bovine Serum Albumin) and 12.5 μg of microsomal protein. The test compound (in sufficient amount to bring the final concentration to from 0.1 to 25 μM), reference compound, or vehicle control is added and the final volume brought to 47 μL. The microtiterplate is then floated on the surface of a 37° C. water bath for fifteen minutes. Incubations are started by the addition of 3 μL $^3$H-acyl CoA (1 μCi/well, final concentration of 10 μM acyl CoA). The plate is then returned to the water bath for 15 minutes. The incubations are then terminated by application of 15 μL from each incubation to individual lanes on a thin layer plate (Silica Gel GF 20×20 cm). Standards are applied to several lanes so that the cholesterol ester band can be identified. After drying, the plates are eluted with 90:10:1 petroleum ether:ether:HOAc. The standards are visualized via iodine vapor, and the regions corresponding to cholesterol ester are scraped into 7 mL scintillation vials. 4 mL of scintillant are added to each vial, and the radioactivity quantified. Background count is determined by the boiled controls. Full activity is determined by activity in the presence of vehicle. The percent inhibition is calculated by subtracting the background from both control and test samples, and the test value is calculated as a percentage of the control. For IC$_{50}$ determinations, the inhibition is plotted against drug doses on a log scale and the concentration at which 50% inhibition is obtained is determined.

In Vivo Assay of Hypolipidemic Agents Using the Hyperlipidemic Hamster

Hamsters are separated into groups of six and given a control cholesterol diet (Pudna Chow #5001 containing 0.5% cholesterol) for seven days. Diet consumption is monitored to determine dietary cholesterol exposure in the face of test compounds. The animals are dosed with the test compound once daily beginning with the initiation of diet. Dosing is by oral gavage of 0.2 mL of corn oil alone (control group) or solution (or suspension) of test compound in corn oil. All animals moribund or in poor physical condition are euthanized. After seven days, the animals are anesthetized by 1M injection of ketamine and sacrificed by decapitation. Blood is collected into vacutainer tubes containing EDTA for plasma lipid analysis and the liver excised for tissue lipid analysis. Data is reported as percent reduction of lipid versus control.

The present invention also relates to a pharmaceutical composition comprising a compound of this invention and a pharmaceutically acceptable carrier. The compounds of formula I can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrates, buffers, preservatives, anti-oxidants, lubricants, flavorings, thickeners, coloring agents, emulsifiers and the like.

The daily hypocholesterolemic or hypolipidemic dose of a compound of formula I is about 7 to about 30 mg/kg of body weight per day. For an average body weight of 70 kg, the dosage level is therefore from about 500 to about 2000 mg of drug per day, given in a single dose or 2–4 divided doses. The exact dose, however, is determined by the attending clinician and is dependent on the potency of the compound administered, the age, weight condition and response of the patient.

Following are preparations of starting materials and examples of preparing compounds of formula I.

Preparation 1

2-(4'-methoxyphenyl)-1-indanone

Step A Dissolve benzaldehyde (489 mL, 4.816 mol) and p-methoxyphenylacetonitrile (598 mL, 4.414 mol) in 95% EtOH (1.5 L). Stir the solution at room temperature while adding 40% aqueous KOH (489 g, 8.732 mol, in 863 mL water) in 2.2 L of 95% EtOH. Stir the mixture for an additional 1.5 h at room temperature, then collect the crystals by suction filtration, wash with water and cold 95% EtOH, and air dry. The weight of the white, crystalline product (mp 92°–94° C., lit. 112° C.) is 999.4 g (96.3%).

Step B Suspend the product of step A (16.01 g, 68.13 mmol) in absolute EtOH (200 mL) at 60°–70° C. under N$_2$. Add solid NaBH$_4$ (2.589 g, 68.13 mmol) in portions over 10 min, and stir the mixture at the same temperature for 2 h. Cool the reaction mixture to ambient temperature and quench with water. Pour the mixture into a volume of water and acidify with conc. HCl. Extract the product into two portions of ether. Combine the organic layers, wash with water and brine, then dry over anhydrous Na$_2$SO$_4$. Filter the product solution and evaporate to give the crude product (15.88 g, 98.4%), mp 66°–67° C. (lit. 104° C.), which can be used without further purification. Alternatively, isolate the product by diluting the crude reaction mixture with several volumes of water, and collect the resulting precipitate by suction filtration (99%).

Step C Combine the product of step B (932.8 g, 3.94 mol) and ethylene glycol (9 L), add a solution of KOH (673 g, 12.02 mol) in water (2.1 L), and heat the mixture at reflux overnight (internal temperature: 120° C.). Cool the reaction mixture, pour into water, and extract twice with diethyl ether. Acidify the aqueous phase with conc. HCl and extract with two portions of ether. Combine the latter organic extracts, wash with brine, dry over Na$_2$SO$_4$, filter and evaporate. Dissolve the crude product in CH$_2$Cl$_2$ and dilute with hexane to induce crystallization. Collect the crystals by suction filtration, wash with hexane/EtOAc (5:1) and hexane, and air dry. Yield: 943.8 g (93.7%), mp 107°–109° C. (lit. 114° C.).

Step D Dissolve the product of step C (64.14 g, 0.251 mol) in 400 mL of CH$_2$Cl$_2$ in a 1 L flask under N$_2$. Treat the solution with three drops of DMF, then add oxalyl chloride (55 mL, 0.626 mol), via syringe. Stir the mixture overnight at room temperature, evaporate, dilute with dry CH$_2$Cl$_2$, and evaporate again. Dissolve the residue in dry CH$_2$Cl$_2$ (100 mL) and add the solution, via dropping funnel (over 5 h), to a suspension of AlCl$_3$ in dry, ice cold CH$_2$Cl$_2$ (800 mL) under N$_2$. Following the addition, stir the mixture for 15 min at 0° C., then pour into water and extract three times with ether. Combine the organic layers, wash successively with water, dilute K$_2$CO$_3$ solution, and brine, then dry over Na$_2$SO$_4$. Filter the product solution and evaporate, then crystallize the resulting residue from EtOH (3 mL/g) to give the title compound (51.3 g, 86%), mp 83°–85° C. (lit. 79°–81° C.).

Using a similar procedure, the following compounds can also be prepared:

2-(3'-nitrophenyl)indanone, mp 115°–118° C.;
2-(4'-nitrophenyl)indanone, mp 145°–148° C.; and
2-phenyl-5-methoxy-indanone, ms 238 (100).

Preparation 2

2-(4'-methoxyphenyl)-1,2,3,4-tetrahydronaphthalen-1-one

Step A Add 10% aqueous NaOH (38 mL) to a solution of p-anisaldehyde (25 mL, 0.206 mol) and acetophenone (23.97 mL, 0.206 mol) in EtOH (500 mL). Stir the mixture at room temperature over night. Dilute the mixture with water and extract with ether. Combine the ethereal extracts, wash with water and brine, dry over $Na_2SO_4$ and concentrate to a solid. Recrystallize the solid from ether/hexanes to provide 27.51 g (56%) of 4'-methoxychalcone, mp 72°–74° C.

Step B Add KCN (11.27 g, 0.173 mol) in water (25 mL) to a 100° C. solution of 4'-methoxychalcone (27.51 g 0.115 mol) and HOAc (7.5 mL, 0.128 mol) in 2-methoxyethanol (200 mL). The reaction is complete in <10 min. Cool the resulting solution to room temperature and pour into a mixture of ice and water (1 L). Extract the mixture with EtOAc. Combine the organic extracts, wash with water and brine, dry over $Na_2SO_4$, filter and concentrate in vacuo. Recrystallize the resulting solid from $CH_2Cl_2$/MeOH to provide 23.07 g (75%) of 2-(4'-methoxyphenyl)-4-phenyl-3-oxobutyronitrile, mp 115°–116° C.

Step C Add a solution of NaOH (34.56 g, 863.9 mmol) in water (375 mL) to a solution of 2-(4'-methoxyphenyl)-4-phenyl-4-oxobutyronitrile (22.92 g, 86.39 mmol) in EtOH (160 mL). Heat the resulting mixture to reflux under nitrogen and monitor the progress of the hydrolysis by TLC (30% EtOAc/hexane, Ce stain). When all of the starting nitrile is consumed, after ~5 h, cool the reaction to room temperature. Dilute the solution with water (1 L), and stir while acidifying with 10% aqueous HCl (pH ~1–2). Collect the resulting precipitate via vacuum filtration, wash with water and air dry to provide 39.43 g of a solid. Dissolve most of the solid in a mixture of $CH_2Cl_2$/MeOH/EtOAc. Vacuum filter through celite, then concentrate the filtrate to a solid and recrystallize from $CH_2Cl_2$/hexanes to provide 18.27 g (74.4%) of 2-(4'-methoxyphenyl)-4-phenyl-4-oxo-butyric acid, mp 157°–158° C.

Step D Dissolve 2-(4'-methoxyphenyl)-4-phenyl-4-oxobutyric acid (18.07 g, 63.55 mmol) in a mixture of MeOH (~25 mL) and HOAc (125 mL). Purge the resulting solution with nitrogen. Add 10% Pd/C (2 g) and hydrogenate on a Parr apparatus over night at ~55 psi. Vacuum filter the mixture through celite. Thoroughly wash the filter cake with 25% MeOH/$CH_2Cl_2$ (300 mL). Concentrate the filtrate in vacuo to give 18.08 g of a solid, and recrystallize from ether/hexanes to provide 12.8 g (74.6%) of 2-(4'-methoxyphenyl)-4-phenylbutyric acid, mp 92°–97° C.

In a manner similar to that in preparation 1, step D, treat 2-(4'-methoxyphenyl)-4-phenylbutyric acid to obtain the title compound, mp 107°–107.5° C.

The following compounds can be prepared using a similar procedure:
2-(2'-methoxyphenyl)-1-tetralone, ms=253 (M+1); and
2-(3'-methoxyphenyl)-1-tetralone, mp 86°–87° C.

Preparation 3

2-(3'-methoxyphenyl)-1-indanone

Step A Prepare a solution of sodium ethoxide using sodium (10.12 g, 0.44 mol) and 200 mL of absolute EtOH under $N_2$. Rapidly add to this solution, a mixture of phthalide (29.5 g, 0.22 mol) and m-anisaldehyde (30 g, 0.22 mol) in 100 mL of EtOH. Heat the reaction mixture to 85° C. and stir at this temperature overnight. Cool to room temperature, acidify carefully with concentrated HCl, then add water to precipitate the product. Collect the precipitate by filtration, wash with water, and air dry to give 34.15 g of the product (61.6%), mp 144°–146° C.

Step B Dissolve the product from step A (3.01 g, 11.94 mmol) in EtOH (200 mL) under $N_2$ and treat with ammonium acetate (17.98 g, 233 mmol). Heat mixture at reflux for 4 h and then cool to room temperature. Add zinc dust (7.5 g, 115 mmol) and heat the mixture at reflux for 2.5 h more. Filter the yellow reaction mixture while hot, and dilute the filtrate with water until cloudy. Allow the filtrate to stand in the freezer overnight. Collect the resulting crystals by filtration, wash successively with cold 6N HCl and water, and dry to obtain the title compound (1.45 g, 51.0%), mp 144°–146° C.

Preparation 4

2-phenyl-1,2,3,4-tetrahydronaphthalen-1-one

Step A Bubble chlorine gas through a 0° C. solution of 1-tetralone (93 mL, 0.70 mol) in $CH_2Cl_2$ (500 mL). Closely monitor the reaction by TLC (50% $CH_2Cl_2$/hexane). When all of the 1-tetralone is consumed, wash the reaction mixture successively with saturated $NaHCO_3$, water and brine, dry over $Na_2SO_4$ and concentrate to an oil. Dissolve the oil in ether (150 mL) and place in the freezer. Collect the resulting crystals via vacuum filtration and wash with cold hexane. Dry the crystals in vacuo to afford 73.26 g of a solid. Chromatograph 10.8 g of the solid on silica gel, using 50% $CH_2Cl_2$/hexane to elute the column, to obtain 7.51 g of 2-chloro-1,2,3,4-tetrahydronaphthalen-1-one.

$^1$H NMR (CDCl$_3$, 200 MHz): δ 8.09 (1H, d, J=5.2 Hz); 7.53 (1 H, dt, J=4.9, 0.9 Hz); 7.36 (1H, t, J=5.2 Hz); 7.28 (1H,d,J=5.0 Hz); 4.64 (1H,dd,J=2.6, 5.2 Hz); 3.29 (1H, m); 3.00 (1H, m); 2.59 (1 H, m); 2.46 (1H, m).

Step B Dry 1.85 g (7.51 mmol) of finely ground cerium trichloride heptahydrate at 140° C. for 2.5 h under vacuum. Cool to room temperature under $N_2$ and add THF (10 mL). Stir the resulting suspension for ~20 h, then cool to 0° C. and treat with phenylmagnesium bromide (3.76 mL, 7.51 mmol, 2M in THF). Stir the mixture at 0° C. for 1.5 h and then cool to −78° C. Add a −78° C. solution of 0.94 g (5.2 mmol) of 2-chloro-1-tetralone in THF (10 mL) via cannula. Warm the mixture to 0° C. and quench the mixture by adding saturated NH$_4$Cl (aqueous). Add 1M aqueous HCl to dissolve any residual salts. Extract with ether, combine the ethereal extracts, wash with water and brine, dry over Na$_2$SO$_4$ and concentrate to give 1.54 g of an oil. Chromatograph on silica gel (50% $CH_2Cl_2$/hexane ) to provide 1.38 g of 2-chloro-1-phenyl-1,2,3,4-tetrahydronaphth-1-ol.

$^1$H NMR (CDCl$_3$, 200 MHz): δ 7.23 (9H, m); 4.66 (1H, dd, J=31., 6.5 Hz); 3.22 (2H, m); 2.92 (1H, dt, J=5.8, 17.2 Hz); 2.22 (2H, m).

Step C Add ethylmagnesium bromide (1.76 mL, 5.27 mmol, M in) dropwise to a 0° C. solution of 2-chloro-1-phenyl-1,2,3,4-tetrahydronaphth-1-ol (1.36 g, 5.27 mmol) in dry benzene (20 mL). Stir the solution at 0° C. for 30 min and heat to reflux for 5 hours. Cool the mixture to room temperature and quench with saturated NH$_4$Cl (aqueous). Extract with ether, combine the ethereal extracts, wash with water and brine, dry over Na$_2$SO$_4$ and concentrate to provide 1.1 g (94%) of the title compound.

$^1$H NMR (CDCl$_3$, 200 MHz): δ 8.10 (1H, d, J=7.8 Hz); 7.51 (1H, dt, J=1.6, 7.4 Hz); 7.29 (5H, m); 7.19 (2H, m); 3.80 (1H, t, J=8 Hz); 3.09 (2H, m); 2.44 (2H, m).

Preparation 5

2-phenylbenzosuberone

Step A Heat a mixture of benzosuberone (12.34 g, 77.02 mmol), isopropenyl acetate (17.8 mL, 161.7 mmol) and pTSA (0.146 g, 0.77 mmol) at reflux overnight (~20 h). Distill the mixture, discarding the fraction distilling from 60°-90° C. Cool the pot residue to room temperature and pour it into a rapidly stirred 1:1 mixture of diethyl ether and aqueous NaHCO$_3$ (saturated). Separate and discard the aqueous layer, then wash the ether layer successively with aqueous NaHCO$_3$ (sat.), water and brine, dry over Na$_2$SO$_4$ and concentrate to a solid 15.42 g (99%), mp 58.5°-60° C.

Step B Combine the product of step A (30.18 g, 149.2 mmol), tri-n-butyltin methoxide (43 mL, 149.2 mmol), palladium acetate (0.336 g, 1.492 mmol), tri-o-tolylphosphine (0.908 g, 2.984 mmol), p-bromoanisole (19 mL, 149.2 mmol) and anhydrous toluene (300 mL), and heat the mixture to 100° C. overnight. Cool to room temperature and add 5 volumes of EtOAc and 250 mL of 2.5M KF (aq.). Stir the mixture overnight and vacuum filter. Wash the filtrate with water and brine, dry over Na$_2$SO$_4$ and concentrate to an oil. Vacuum distill the oil to remove 23.7 g of unidentified material. Discontinue the distillation when the enolacetate crystallizes in the condenser. Chromatograph the pot residue on silica gel using 10% EtOAc/hexane to obtain 17.89 g (45%) of the title compound, ms=267 (M+).

The following compounds can be prepared using a similar procedure:

| Compound # | R$^2$ | Ar$^2$ | Y | n | physical data |
|---|---|---|---|---|---|
| 5A | 6-CH$_3$O | C$_6$H$_5$ | CH$_2$ | 1 | mp 116-117° C. |
| 5B | H | C$_6$H$_5$ | O | 1 | mp 76-77° C. |
| 5C | H | 4-aminophenyl | CH$_2$ | 1 | ms=237(M+) |
| 5D | H | 4-CH$_3$O—phenyl | CH$_2$ | 1 | mp 107-107.5° C. |
| 5E | 7-CH$_3$O | C$_6$H$_5$ | CH$_2$ | 1 | mp 74-75° C. |
| 5F | 5-CH$_3$O | C$_6$H$_5$ | CH$_2$ | 1 | mp 81-82° C. |
| 5G | 7-CH$_3$O | 4-CH$_3$O—phenyl | CH$_2$ | 1 | mp 92-93° C. |

Preparation 6

2-(4'-pyridyl)-1,2,3,4-tetrahydronaphthalen-1-one

Step A Add 30 mL of 50% NaOH (aq.) to a mixture of phenethylbromide (13.23 mL, 97.0 mmol), 4'-pyridylacetonitrile hydrochloride salt (15.0 g, 97 mmol) and triethylbenzylammonium chloride (0.34 g, 1.49 mmol) and stir the mixture overnight. Partition the reaction mixture between EtOAc and water, then extract with EtOAc. Combine the organic extracts, wash with water and brine, dry over Na$_2$SO$_4$ and concentrate to a residue. Vacuum distill the residue collecting the product 4-phenyl-2-(4'-pyridyl)butyronitrile at 160°-200° C. (13.32 g, 62%), ms=222 (M+)

Step B Combine 4-phenyl-2-(4'-pyridyl)butyronitrile (0.61 g, 2.68 mmol), NaCl (3.13 g, 53.6 mmol) and AlCl$_3$ (14.29 g, 107.2 mmol) and heat to 180° C. After 30 minutes, cool the reaction mixture to 0° C. and pour it into water. Add 15% NaOH (aqueous) until the solution is clear and basic. Extract with ether, combine the ethereal extracts, wash with water and brine, dry over Na$_2$SO$_4$, and concentrate to a residue. Chromatograph the residue on silica gel using 100% EtOAc to obtain 0.45 g (75%) of the title compound, mp 87°-90° C.

Preparation 7 trans-2-(4'-methoxyphenyl)-1,2,3,4-tetrahydronaphthyl-1-amine

Step A Add DIBAL-H (83.8 mL, 83.8 mmol, 1M in THF) dropwise to a −78° C. solution of 2-(4'-methoxyphenyl)-1,2,3,4-tetrahydronaphthalen-1-one (7.15 g, 27.94 mmol) in anhydrous THF (150 mL). Allow the reaction to come to room temperature overnight. Cool the mixture to 0° C. and quench with sodium sulfate decahydrate. Stir the mixture overnight, then vacuum filter and thoroughly wash the filtercake with THF. Concentrate the filtrate in vacuo, then chromatograph the resulting oil on silica gel using 20% EtOAc/hexanes to give a solid. Recrystallize from EtOAc/hexane to obtain 4.84 g (67%) of 2-(4'-methoxyphenyl)-1,2,3,4-tetrahydronaphthalen-1-ol, mp 89°-90.5° C.

Step B Add Ph$_3$P (4.54 g, 17.3 mmol) to a −20° C. (dry ice/carbon tetrachloride) solution of 2-(4'-methoxyphenyl)-1,2,3,4-tetrahydronaphthalen-1-ol (3.52 g, 13.84 mmol) in THF (100 mL). Add DEAD (3.05 mL, 19.4 mmol) dropwise to the mixture, followed by addition of diphenylphosphoryl azide (3.72 mL, 17.3 mmol) in the same manner. Allow the mixture to warm to room temperature overnight. Concentrate the reaction mixture to a residue and chromatograph the residue on silica gel using 20% EtOAc/hexane to obtain 3.46 g of an oil containing the desired trans-2-(4'-methoxyphenyl)-1,2,3,4-tetrahydronaphtha-1-azide (TLC: Rf=0.42 (20% EtOAc/hexane), yellow, Ce stain).

Dissolve the oil in EtOH (150 mL), purge with nitrogen and add 10% Pd/C (0.35 g). Hydrogenate the suspension on a Parr apparatus at 55 psi overnight. Filter the mixture through celite and thoroughly wash the filter cake with 25% MeOH/CH$_2$Cl$_2$ (300 mL). Concentrate the filtrate in vacuo to a residue and chromatograph on silica gel using 5% MeOH/CH$_2$Cl$_2$ to give 1.99 g of the title compound, ms=254 (M+1).

Using a similar procedure, the following compounds can also be prepared:

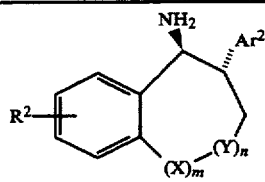

| Compound # | Ar² | R² | X | Y | m | n | physical data |
|---|---|---|---|---|---|---|---|
| 7A | 2-methoxyphenyl | H | — | CH₂ | 0 | 1 | ms=254(M⁺1) |
| 7B | 3-methoxyphenyl | H | — | — | 0 | 0 | ms=239(M+) |
| 7C | 3-methoxyphenyl | H | — | CH₂ | 0 | 1 | ms=254(M⁺1) |
| 7D | C₆H₅ | H | — | O | 0 | 1 | ¹H NMR: δ 7.66(1H, d, J=7.6Hz); 7.40(3H, m); 7.32(3H, m); 7.04(1H, t, J=7.3Hz); 6.94 (1H, d, J=8.6Hz); 4.41(1H, dd, J=3.8, 11.2 Hz); 4.29(2H, m); 3.05(1H, dt, J=9.6, 3.7 Hz); 2.21(2H, br s). |
| 7E | 4-methoxyphenyl | H | — | — | 0 | 0 | ms 239(M+) |
| 7F | 4-methoxyphenyl | H | CH₂ | CH₂ | 1 | 1 | mp 82–82.5° C. |
| 7G | 4-pyridyl | H | — | CH₂ | 0 | 1 | mp 87–88° C. |
| 7H | C₆H₅ | 6-CH₃O— | — | — | 0 | 0 | ¹H NMR: δ 7.38–7.15(m, 6H); 6.88–6.77 (m, 2H); 4.32(d, J=9.7Hz, 1H); 3.79(s, 3H); 3.24–2.98(m, 3H); 1.13(br s, 2H) |
| 7I | C₆H₅ | 7-CH₃O— | — | CH₂ | 0 | 1 | mp 140–141° C. |
| 7J | C₆H₅ | 5-CH₃O— | — | CH₂ | 0 | 1 | mp 130–131° C. |
| 7K | C₆H₅ | 6-CH₃O— | — | CH₂ | 0 | 1 | IR(KBr)3431, 3243, 1593, 1546 cm⁻¹ |
| 7L | 4-methoxyphenyl | 7-CH₃O— | — | CH₂ | 0 | 1 | mp 79–80° C. |

Preparation 8 cis-2-(4'-methoxyphenyl)-1,2,3,4-tetrahydronaphthyl-1-amine

Step A Heat a mixture of 2-(4'-methoxyphenyl)-1,2,3,4-tetrahydronaphthalen-1-one (6.22 g, 24.7 mmol), hydroxylamine hydrochloride (5.14 g, 74 mmol), NaOAc (6.1 g, 74 mmol), water (12 mL) and MeOH (45 mL) at reflux overnight. Concentrate the reaction mixture to approximately 50% of its original volume, dilute with water and cool to room temperature. Partition between EtOAc and water and extract the aqueous phase with EtOAc. Combine the organic extracts, wash with water and brine, dry over Na₂SO₄, and concentrate to a residue. Chromatograph the residue on silica gel using 15% EtOAc/hexane, then recrystallize from EtOAc/hexanes to obtain the desired oxime, mp 124°–125° C.

Step B Add a solution of chlorodiphenylphosphine (3.98 mL, 22.2 mmol) in CH₂Cl₂ (20 mL), via cannula, to a −40° C. solution of the oxime from step A (5.93 g, 22.2 mmol) and Et₃N (3.1 mL, 22.2 mmol) in a 1:1 mixture of CH₂Cl₂/petroleum ether (50 mL each). Allow the reaction mixture to slowly warm to room temperature (~2 h). Analyze the reaction mixture by TLC (50% EtOAc/hexane) to check for the presence of starting material. If starting material remains, re-cool the reaction mixture to −40° C. and treat with Et₃N (0.62 mL, 4.4 mmol) and chlorodiphenylphosphine (0.80 mL, 4.4 mmol). Again allow the mixture to warm to room temperature. Filter the solution and concentrate the filtrate in vacuo to a foam. Dissolve the foam in benzene, dry over Na₂SO₄, filter and concentrate in vacuo to isolate the phosphinylimine (11.48 g, ~115% crude yield).

Dissolve the phosphinylimine (10.32 g, 22.9 mmol) in dry THF (200 mL) and cool to −78° C. Add DIBAL-H (68.6 mL, 68.6 mmol, 1M in THF) slowly via syringe. The reaction is complete in <10 min. Quench at −78° C. by the addition of solid sodium sulfate decahydrate and allow the mixture to warm slowly to room temperature. Filter the mixture and thoroughly wash the filter cake with THF. Concentrate the filtrate and recrystallize from benzene/hexane to give the phosphonamide, mp 204°–204.5° C.

Step C Add 6N aqueous HCl (100 mL) to a room temperature solution of the phosphonamide from step B (8.68 g, 19.1 mmol) in MeOH (300 mL). Stir the mixture overnight, then concentrate the mixture in vacuo and partition the residue between 3N HCl and EtOAc. Extract with EtOAc, reserving the organic extracts. Adjust the pH of the aqueous layer to pH ~9 with aqueous Na₂CO₃ (saturated). Extract with CH₂Cl₂, combine the CH₂Cl₂ extracts, wash with water, dry over Na₂SO₄ and concentrate to give the title compound (2.73 g, 56%). Analyze the original EtOAc extracts by TLC to check for some of the desired amine. Combine these extracts, stir with aqueous Na₂CO₃ (saturated), wash successively with Na₂CO₃ (saturated), water and brine, then concentrate to a residue. Chromatograph the residue on silica gel with 50% EtOAc/hexane containing 1% Et₃N to obtain an additional 1.24 g of the desired amine. Total yield for the reaction is 3.97 g (82%) of the title compound, ms=254 (M+1).

The following compounds can be prepared using a similar procedure:

cis-2-phenyl-1,2,3,4-tetrahydronaphthyl-1-amine, ms=224 (M+1);
cis-6-methoxy-2-phenyl-1,2,3,4-tetrahydronaphthyl-1-amine, mp 177°-178° C.;
cis-2-(3'-methoxyphenyl)-1,2,3,4-tetrahydronaphthyl-1-amine, ms=254 (M+1);
cis-5-methoxy-2-phenyl-1,2,3,4-tetrahydronaphthyl-1-amine, ms=254 (M+1);
cis-7-methoxy-2-phenyl-1,2,3,4-tetrahydronaphthyl-1-amine, mp 70°-71° C.;
cis-7-methoxy-2-(4'-methoxyphenyl)-1,2,3,4-tetrahydronaphthyl-1-amine, ms=283 (M+).

Preparation 9 cis-2-(4'-methoxyphenyl)benzosuberamine

Step A Slowly add NaBH$_4$ (1.84 g, 48.7 mmol) in small portions to a 0° C. solution of 2-(4'-methoxyphenyl)benzo-suberone (4.32 g, 16.2 mmol) in MeOH (75 mL). Allow the mixture to stir until gas evolution ceases (~10 min). Quench by the addition of aqueous 3N HCl (10 mL). Remove most of the solvent in vacuo. Partition the residue between 3N HCl and EtOAc. Extract with EtOAc, then combine the extracts, wash with water and brine, dry over anhydrous Na$_2$SO$_4$ and concentrate to 3.7 g. of an oil.

Dissolve the oil in toluene (75 mL), add pTSA (0.31 g, 0.16 mmol) and heat the mixture at reflux overnight, removing the water as an azeotrope. Cool the mixture to room temperature, dilute with EtOAc, and extract with EtOAc. Combine the extracts, wash successively with aqueous Na$_2$CO$_3$ (sat.), water and brine, dry over Na$_2$SO$_4$ and concentrate to a residue. Crystallize from ether/hexane to provide the desired olefin, mp 80°-81° C.

Step B Add borane THF complex (27.6 mL, 27.6 mmol, 1M in THF) to a 0° C. solution of the olefin from step A (3.14 g, 12.5 mmol) in THF (50 mL). Allow the solution to warm to room temperature overnight. Cool the solution to 0° C. and add 3N aqueous NaOH (28 mL), then slowly add 30% H$_2$O$_2$ (28 mL). Stir the resulting mixture overnight, then extract with EtOAc. Combine the extracts, wash successively with aqueous NaHCO$_3$ (saturated), water and brine, dry over Na$_2$SO$_4$, filter and concentrate to a solid. Recrystallize the solid from EtOAc/hexane to afford the desired alcohol, mp 87.5°-88.5° C.

In a manner similar to that in preparation 7, step B, the alcohol from step B is converted to the title compound, ms=267 (M+).

Using a similar procedure, cis-2-(2'-methoxyphenyl)-1,2,3,4-tetrahydronaphthylamine, ms=254 (M+1), can also be prepared.

Preparation 10

2-(4'-methoxyphenyl)indanamine

Step A Combine 2-(4'-methoxyphenyl)indanone (67.81 g, 285 mmol), methoxylamine hydrochloride (35.69 g, 427 mmol), NaOAc (35.04 g, 427 mmol), and MeOH (750 mL) under N$_2$. Stir the mixture at 60°-65° C. for 5 h, then overnight at room temperature. Pour the reaction mixture into two volumes of water and extract three times with 1:1 hexane/EtOAc. Wash the combined extracts with water and brine, and dry over Na$_2$SO$_4$. Filter the mixture and evaporate the solvent to obtain the oxime methyl ether (72.1 g, 100%).

Step B Treat the oxime methyl ether from step A (72.1 g, 285 mmol) with 1M borane in THF (700 mL, 700 mmol) under N$_2$. Stir the mixture at room temperature overnight, then at reflux for 5 h. Cool the reaction mixture, and quench the excess borane with water. When bubbling ceases, bring the mixture to ca. pH 1 with concentrated HCl, stir vigorously at 50° C. for 2 h, then stir at room temperature for 5 h more. Pour the mixture into water and extract twice with diethyl ether. Basify the aqueous phase to pH 9-10 with KOH and extract three times with ether. Combine the latter organic extracts, wash with brine and dry with Na$_2$SO$_4$. Filter the solution and evaporate the solvent to give the title compound as a mixture of cis and trans isomers (ca. 10:1). Filter the crude product through silica gel (EtOAc) to partially purify the title compound, ms=239 (M+).

Using a similar procedure, the following compounds can also be prepared:

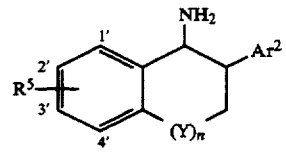

| Compound # | Ar$^2$ | R$^5$ | Y | n | physical data |
|---|---|---|---|---|---|
| 10A | cis-3-methoxyphenyl | H | — | 0 | ms=239(M+) |
| 10B | cis-3-nitrophenyl | H | — | 0 | $^1$H NMR: δ 8.10(m, 2H); 7.58-7.24(m, 6H); 4.67 (d, J=4.5Hz, 1H); 3.83 (dd, J=8.0, 4.5Hz, 1H); 3.40-3.22(m, 2H); 1.18 (br s, 2H) |
| 10C | cis-4-nitrophenyl | H | — | 0 | ms=254(M+) |
| 10D | cis-C$_6$H$_5$ | 3'-MeO | — | 0 | $^1$H NMR: δ 7.38-7.16(m, 6H); 6.88-6.76(m, 2H); 4.49(d, J=6.8Hz, 1H); 3.81(s, 3H); 3.72(app q, J=7.2Hz, 1H); 3.21(ddd, J=15.4, 7.7, 7.2Hz, 2H); 1.14(br s, 2H) |
| 10E | cis-C$_6$H$_5$ | H | O | 1 | |
| 10F | trans-3-nitrophenyl | H | — | 0 | $^1$H NMR: δ 8.29(m, 1H); 7.74(d, J=6.3Hz, 1H); 7.57-7.24(m, 6H); 4.42(d, J=6.5Hz, 1H); 3.31-3.05(m, 3H); 1.19 (br s, 2H) |
| 10F | trans-4-nitrophenyl | H | — | 0 | ms=254(M+) |
| 10G | cis-C$_6$H$_5$ | 2'-MeO | — | 0 | $^1$H NMR: δ 7.30-7.00 (m, 6H); 6.85 (d, 1H, J=1Hz); 6.72(dd, 1H, J=1.4Hz); 3.72(s, 3H); 3,62 (m, 1H); 3.10(m, 2H). |

Preparation 11

Resolution of 2-(4'-methoxyphenyl)indanamine

Dissolve the title amine (racemic), obtained from preparation 10, step B, in 2.5 L hot EtOH. Slowly add a hot solution of 100 g di-p-toluoyl-D-tartaric acid in EtOH (500 mL), and allow the solution to stand at room temperature overnight. Collect the crystals and wash with EtOH and 1:1 hexane:ether. Concentrate the filtrate under vacuum to ca. 500 mL then basify with NaOH. Extract with three 1 L portions of ether. Wash the combined ether layers with brine and dry over Na$_2$-

SO₄. Filter the solution, evaporate the solvent, dissolve the residue in 1 L of hot EtOH and treat with a hot solution of 55 g of di-p-toluoyl-L-tartaric acid in 700 mL EtOH. Allow the solution to stand overnight at room temperature and collect the crystals using the procedure described above to give 63 grams of a single enantiomer of the title compound.

The opposite enantiomer can be similarly prepared by using di-p-toluoyl-D-tartaric acid and di-p-toluoyl-L-tartaric acid in the reverse order.

Wash with water, dry over Na₂SO₄ and concentrate in vacuo to a solid. Recrystallize from CH₂Cl₂/hexanes to give 2.92 g (84%) of the title compound, mp 215°-215.5° C.

Using a similar procedure, the following compounds can also be prepared:

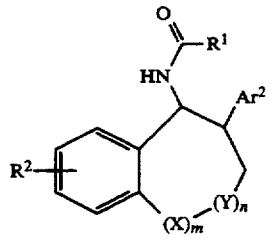

| Compound # | Ar² | R² | —CR¹ (O) | cis or trans | X | Y | m | n | physical data |
|---|---|---|---|---|---|---|---|---|---|
| 1A | 2-methoxyphenyl | H | 2,2-diphenylacetyl | cis | — | CH₂ | 0 | 1 | mp 215-216° C. |
| 1B | 2-methoxyphenyl | H | 2,2-diphenylacetyl | trans | — | CH₂ | 0 | 1 | mp 216-217° C. |
| 1C | 3-methoxyphenyl | H | 2,2-diphenylacetyl | cis | — | CH₂ | 0 | 1 | mp 138-139° C. |
| 1D | 3-methoxyphenyl | H | 2,2-diphenylacetyl | trans | — | CH₂ | 0 | 1 | mp 213-214 |
| 1E | C₆H₅ | H | 2,2-diphenylacetyl | cis | | O | 0 | 1 | mp 169.5-170° C. |
| 1F | 4-methoxyphenyl | H | 2,2-dimethylundecan-oyl | trans | — | CH₂ | 0 | 1 | mp 74-75° C. |
| 1G | 4-methoxyphenyl | H | 2,2-diphenylacetyl | trans | — | CH₂ | 0 | 1 | mp 251-252° C. |
| 1H | 4-methoxyphenyl | H | 2,2-diphenylacetyl | cis | CH₂ | CH₂ | 1 | 1 | mp 155-156° C. |
| 1I | 4-methoxyphenyl | H | 2,2-diphenylacetyl | trans | CH₂ | CH₂ | 1 | 1 | mp 235-235.5° C. |
| 1J | 4-pyridyl | H | 2,2-diphenylacetyl | trans | — | CH₂ | 0 | 1 | mp 237.5-238° C. |
| 1K | C₆H₅ | 6-MeO— | 2,2-diphenylacetyl | cis | — | CH₂ | 0 | 1 | mp 188-189° C. |
| 1L | C₆H₅ | 6-MeO— | 2,2-diphenylacetyl | trans | — | CH₂ | 0 | 1 | mp 259-260° C. |
| 1M | C₆H₅ | H | 2,2-diphenylacetyl | trans | — | O | 0 | 1 | mp 217-219° C. |
| 1N | C₆H₅ | 7-MeO— | 2,2-diphenylacetyl | cis | — | CH₂ | 0 | 1 | mp 198-199° C. |
| 1O | C₆H₅ | 7-MeO— | 2,2-diphenylacetyl | trans | — | CH₂ | 0 | 1 | mp 266-268° C.(dec.) |
| 1P | C₆H₅ | 5-MeO— | 2,2-diphenylacetyl | cis | — | CH₂ | 0 | 1 | mp 217-218° C. |
| 1Q | C₆H₅ | 5-MeO— | 2,2-diphenylacetyl | trans | — | CH₂ | 0 | 1 | mp 238-239° C. |
| 1R | 4-methoxyphenyl | 7-MeO | 2,2-diphenylacetyl | trans | — | CH₂ | 0 | 1 | mp=258-259° C. |
| 1S | 4-methoxyphenyl | 7-MeO | 2,2-diphenylacetyl | cis | — | CH₂ | 0 | 1 | mp=208-210° C.(dec.) |

EXAMPLE 1 cis-N-[-2-(4'-methoxyphenyl)-1,2,3,4-tetrahydronaphthalen-1-yl]-α-phenylbenzeneacetamide Add diphenylacetyl chloride (2.14 g, 9.28 mmol) to a 0° C. solution of cis-2-(p-methoxyphenyl)-1,2,3,4-tetrahydronaphthyl-1-amine (1.96 g, 7.74 mmol) and Et₃N (1.62 mL, 11.6 mmol) in CH₂Cl₂ (100 mL). Analyze the reaction mixture by TLC (5% MeOH/CH₂Cl₂, Ce stain) to determine when consumption of the the starting amine is complete. Dilute the reaction mixture with water and CH₂Cl₂ and stir until all the solids dissolve.

EXAMPLE 2 cis-N-[2-(4'-methoxyphenyl)indanyl]-α-phenylbenzeneacetamide

Dissolve 1.25 grams of cis-2-(4'-methoxyphenyl)indanamine in CH₂Cl₂ (30 mL) and treat the solution sequentially with HOBT (607 mg, 4.494 mmol), diphenylacetic add (1.143 g, 5.393 mmol), and EDCI (1.033 g, 5.393 mmol). Stir the mixture at room temperature for 1 h, then pour into water and extract twice with 1:1 hexane/EtOAc. Wash the organic phase once with 1N HCl (aq.), twice with aqueous K₂CO₃, and once with brine. Dry the organic solution with Na₂SO₄, then filter and evaporate the filtrate. Flush the resulting residue through a pad of silica gel (1:1 hexane/EtOAc)

and evaporate to give a solid. Purify the solid by preparative, normal phase HPLC (4:1 hexane/EtOAc) to provide 1.077 g of the title compound, mp 168°-170° C.

Using a similar procedure, the following compounds can also be prepared:

times with ether. Combine the ether extracts, wash once with water, twice with aqueous $Na_2S_2O_3$ solution, and once with brine, then dry over $Na_2SO_4$. Filter the ethereal solution and concentrate to a residue. (If the residue is highly colored, filter it through silica gel, eluting first

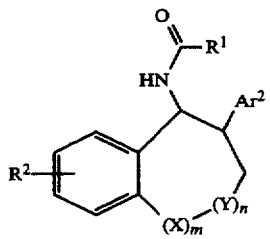

| Compound # | $Ar^2$ | $R^2$ | $-\overset{O}{\underset{\|}{C}}R^1$ | cis or trans | X | Y | m | n | physical data |
|---|---|---|---|---|---|---|---|---|---|
| 2A | 3-methoxy-phenyl | H | 2,2-diphenyl-acetyl | cis | — | — | 0 | 0 | mp 144–146° C. |
| 2B | 3-methoxy-phenyl | H | 2,2-diphenyl-acetyl | trans | — | — | 0 | 0 | mp 169–171° C. |
| 2C | 3-nitro-phenyl | H | 2,2-diphenyl-acetyl | cis | — | — | 0 | 0 | mp 201–203° C. |
| 2D | 3-nitro-phenyl | H | 2,2-diphenyl-acetyl | trans | — | — | 0 | 0 | mp 185–187° C. |
| 2E | $C_6H_5$ | 7-MeO— | 2,2-diphenyl-acetyl | cis | — | — | 0 | 0 | mp 211–212° C. |
| 2F | 4-methoxy-phenyl | H | 2,2-diphenyl-acetyl | trans | — | — | 0 | 0 | 197–199° C. |
| 2G | 4-methoxy-phenyl | H | oleoyl | cis | — | $CH_2$ | 0 | 1 | ms=518 (M+1) |
| 2H | 4-methoxy-phenyl | H | oleoyl | trans | — | $CH_2$ | 0 | 1 | ms 518(M+1) |
| 2I | 4-nitro-phenyl | H | 2,2-diphenyl-acetyl | cis | — | — | 0 | 0 | mp 218–219° C. |
| 2J | 4-nitro-phenyl | H | 2,2-diphenyl-acetyl | trans | — | — | 0 | 0 | mp 215–216° C. |
| 2K | $C_6H_5$ | 5-MeO— | 2,2-diphenyl-acetyl | trans | — | — | 0 | 0 | mp 190–192° C. |
| 2L | $C_6H_5$ | H | oleoyl | cis | — | $CH_2$ | 0 | 1 | ms=488(M+) |
| 2M | $C_6H_5$ | H | oleoyl | trans | — | $CH_2$ | 0 | 1 | ms=488(M+) |
| 2N | $C_6H_5$ | H | oleoyl | cis | — | O | 0 | 1 | mp 88–89° C. |
| 2O | $C_6H_5$ | H | oloeyl | trans | — | O | 0 | 1 | ms=490(M+) |
| 2P | 4-amino-phenyl | H | 2,2-diphenyl-acetyl | trans | — | $CH_2$ | 0 | 1 | mp 229.5–230.5° C. |
| 2Q | $C_6H_5$ | 6-MeO | 2,2-diphenyl acetyl | cis | — | — | 0 | 0 | mp=160–162° C. |
| 2R | $C_6H_5$ | 5-MeO— | 2,2-diphenyl-acetyl | cis | — | — | 0 | 0 | mp=182–184° C. |
| 2S | $C_6H_5$ | H | 2,2-diphenyl-acetyl | cis | — | — | 0 | 0 | mp=172–174° C. |
| 2T | $C_6H_5$ | 6-MeO— | 2,2-diphenyl-acetyl | trans | — | — | 0 | 0 | mp=205–207° C.(dec.) |

EXAMPLE 3 cis-N-[2-(4'-hydroxyphenyl)indanyl]-αphenylbenzeneacetamide

Dissolve cis-N-[2-(4'-methoxyphenyl)indanyl]-α-phenylbenzeneacetamide (27.80 g, 64.20 mmol) in $CH_2Cl_2$ (500 mL) in a flask under $N_2$. Add a solution of $BBr_3$ (1.0M in $CH_2Cl_2$) via syringe until the reaction is complete as determined by TLC analysis. [A total of 160 mL (160 mmol) of the $BBr_3$ solution is required.] Pour the reaction mixture into water and extract three times with ether. Combine the ether extracts, wash once with water, twice with aqueous $Na_2S_2O_3$ solution, and once with brine, then dry over $Na_2SO_4$. Filter the ethereal solution and concentrate to a residue. (If the residue is highly colored, filter it through silica gel, eluting first with $CH_2Cl_2$, and then with $CH_2Cl_2$/ether to purify.) Dissolve the product in $CH_2Cl_2$, dilute with an equal volume of hexane, and heat the mixture to boiling until crystallization commences. Heat the mixture for an additional 10–15 min and then cool to room temperature. Collect the crystals by suction filtration, wash thoroughly with 5:1 hexane/EtOAc, then with hexane, and air dry to provide the title compound (24.68 g, 91.7%), mp 165.5°–167.5° C.

Using similar procedures, the following compounds can also be prepared:

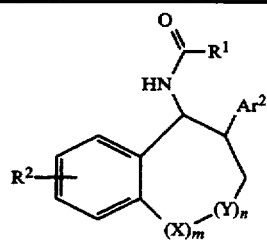

| Compound # | Ar² | R² | —CR¹ (O=) | cis or trans | X | Y | m | n | physical data |
|---|---|---|---|---|---|---|---|---|---|
| 3A | 2-hydroxyphenyl | H | 2,2-diphenylacetyl | trans | — | CH₂ | 0 | 1 | mp 258–259° C. |
| 3B | 3-hydroxyphenyl | H | 2,2-diphenylacetyl | cis | — | — | 0 | 0 | mp 178–180° C. |
| 3C | 3-hydroxyphenyl | H | 2,2-diphenylacetyl | cis | — | CH₂ | 0 | 1 | mp 185–186° C. |
| 3D | 3-hydroxyphenyl | H | 2,2-diphenylacetyl | trans | — | CH₂ | 0 | 1 | mp 207–208° C. |
| 3E | 4-hydroxyphenyl | H | 2,2-diphenylacetyl | trans | — | — | 0 | 0 | mp 188–190° C. |
| 3F | 4-hydroxyphenyl | H | 2,2-diphenylacetyl | cis | — | CH₂ | 0 | 1 | mp 211.5–212° C. |
| 3G | 4-hydroxyphenyl | H | 2,2-diphenylacetyl | trans | — | CH₂ | 0 | 1 | mp 204–206° C. |
| 3H | 4-hydroxyphenyl | H | 2,2-dimethylundecanoyl | trans | — | CH₂ | 0 | 1 | mp 148.5–149° C. |
| 3I | 4-hydroxyphenyl | H | CN(phenyl)₂ (O=) | trans | — | CH₂ | 0 | 1 | mp 213.5–215° C. |
| 3J | 4-hydroxyphenyl | H | 2,2-diphenylacetyl | trans | CH₂ | CH₂ | 1 | 1 | mp 184–185° C. |
| 3K | C₆H₅ | 5-OH | 2,2-diphenylacetyl | cis | — | — | 0 | 0 | mp 171–172° C. |
| 3L | C₆H₅ | 5-OH | 2,2-diphenylacetyl | trans | — | — | 0 | 0 | mp 209–211° C. |
| 3M | C₆H₅ | 6-OH | 2,2-diphenylacetyl | cis | — | CH₂ | 0 | 1 | mp 254–255° C. |
| 3N | C₆H₅ | 6-OH | 2,2-diphenylacetyl | trans | — | CH₂ | 0 | 1 | mp 248–250° C. |
| 3O | 2-hydroxyphenyl | H | 2,2-diphenylacetyl | cis | — | CH₂ | 0 | 1 | mp 267–268° C. |
| 3P | C₆H₅ | 7-OH | 2,2-diphenylacetyl | cis | — | CH₂ | 0 | 1 | mp 177–178° C. |
| 3Q | C₆H₅ | 7-OH | 2,2-diphenylacetyl | trans racemic | — | CH₂ | 0 | 1 | mp 220–222° C.(dec.) |
| 3R | 4-hydroxyphenyl | H | 2,2-diphenylacetyl | cis | CH₂ | CH₂ | 1 | 1 | 196.5–197.5° C. |
| 3S | C₆H₅ | 5-OH | 2,2-diphenylacetyl | trans | — | CH₂ | 0 | 1 | mp 219–220° C. |
| 3T | C₆H₅ | 5-OH | 2,2-diphenylacetyl | cis | — | CH₂ | 0 | 1 | mp 210–211° C. |
| 3U | 4-hydroxyphenyl | 7-OH | 2,2-diphenylacetyl | trans | — | CH₂ | 0 | 1 | mp=241–242° C. |
| 3V | 4-hydroxyphenyl | 7-OH | 2,2-diphenylacetyl | cis | — | CH₂ | 0 | 1 | mp=242–243° C. |
| 3W | C₆H₅ | 6-OH | 2,2-diphenylacetyl | cis | — | — | 0 | 0 | mp=195–197° C. |
| 3X | C₆H₅ | 7-OH | 2,2-diphenylacetyl | cis | — | — | 0 | 0 | mp=146–147° C. |
| 3Y | C₆H₅ | 7-OH | 2,2-diphenylacetyl | (+)-trans isomer | — | CH₂ | 0 | 1 | mp=220–222° C.(dec.) |
| 3Z | C₆H₅ | 7-OH | 2,2-diphenylacetyl | (−)-trans isomer | — | CH₂ | 0 | 1 | mp=220–222° C. |
| 3AA | 4-hydroxyphenyl | H | 2,2-diphenylacetyl | (+)-cis isomer | — | — | 0 | 0 | mp=165–167° C. |
| 3BB | 4-hydroxyphenyl | H | 2,2-diphenylacetyl | (−)-cis isomer | — | — | 0 | 0 | mp=164–165° C. |
| 3CC | C₆H₅ | 8-OH | 2,2-diphenylacetyl | trans | — | CH₂ | 0 | 1 | mp=218–219° C. |

EXAMPLE 4 trans-N-[2-(4'-hydroxyphenyl)-1,2,3,4-tetrahydronaphth-1-yl]oleamide

Prepare a suspension of NaH (0.19 g, 1.34 mmol) in dry DMF (15 mL) and cool to 0° C. Add EtSH (0.69 mL, 9.37 mmol), then stir at room temperature until all of the NaH is consumed. Add a solution of trans-2-(4'-methoxyphenyl)-1,2,3,4-tetrahydronaphthyl-1-amine oleamide (0.69 g, 1.34 mmol) in DMF (10 mL), and heat the mixture at reflux overnight (~17 h). Cool the mixture to room temperature and quench with 1M HCl (aq.). Extract with ether, combine the ethereal extracts, wash with water and brine, dry over Na$_2$SO$_4$ and concentrate to a residue. Chromatograph the residue on silica gel with 30–50% EtOAc/hexanes to obtain a solid. Further purify the solid by HPLC (silica gel, 30% EtOAc/hexane) to give 0.5 g of the title compound (mp 103.5°–107.5° C.).

Using a similar procedure, the cis-isomer (4A) of the title compound, mp 125.5°–126.5° C., can be prepared.

EXAMPLE 5 trans-N-[2-(4'-aminophenyl)indanyl]-α-phenylbenzeneacetamide

Hydrogenate a solution of trans-N-[2-(4'-nitrophenyl)indanyl]-α-phenylbenzeneacetamide (75 mg, 0.167 mmol) in 10 mL EtOH over 5% Pd/C (12 mg) at 60 psi for 2 hours. Filter though celite and concentrate the filtrate to a residue. Purify the residue by chromatography over silica gel with 1:1 hexane/EtOAc, to give 42 mg of the title compound, mp=184°–186° C.

Using a similar procedure, cis-N-[2-(3'-aminophenyl)indanyl]-α-phenylbenzeneacetamide (5A), mp 134°–137° C. can be prepared.

EXAMPLE 6 trans-N'-[2-(4'-methoxyphenyl)-1,2,3,4-tetrahydronaphthalen-1-yl]-N,N-diphenylurea Add triphosgene (0.46 g, 1.55 mmol) to a room temperature solution of trans-2-(4'-methoxyphenyl)-1,2,3,4-tetrahydronaphthyl-1-amine (1.19 g, 4.71 mmol) and Et$_3$N (0.72 mL, 5.18 mmol) in THF (20 mL). After 15 min, add diphenylamine (0.80 g, 4.71 mmol) and heat the mixture at reflux overnight. Cool to room temperature, dilute with water and EtOAc, and extract with EtOAc. Combine the extracts, wash with water and brine, dry over Na$_2$SO$_4$, and concentrate to a residue. Chromatograph the residue on silica gel with 20–60% EtOAc/hexane to provide the title compound 1.14 g (54%), mp 186.5°–187.5° C.

EXAMPLE 7

(+)-cis-N-[2-(3'-bromo-4'-hydroxyphenyl]indanyl]-α-phenylbenzeneacetamide

Add 0.262 g (1.472 mmol) of NBS to the compound of Example 3AA, (0.596 g, 1.422 mmol) in 10 mL of dry DMF at 0° C. Stir the mixture at 0° C. for 30 min. then at room temperature for 4 hours. Pour the mixture into water and extract with EtOAc. Wash the EtOAc extract with water, then dry the extract over Na$_2$SO$_4$. Filter then evaporate the solvent to give a residue. Chromatograph the residue over silica gel (10:1 CH$_2$Cl$_2$/EtOAc) to give 0.479 g of the title compound, mp 158°–159° C.

EXAMPLE 8 cis-N-[2-(3'-chloro-4'-hydroxyphenyl)indanyl]-α-phenylbenzeneacetamide

Dissolve the product of Example 3 (1.0 g) in 30 mL of dry CH$_2$Cl$_2$. Slowly add (dropwise) 0.09 mL of sulfuryl chloride followed by 3 mL of anhydrous ether. Stir the mixture at room temperature for 2 hours, then slowly pour the mixture into ice water. Extract with CH$_2$Cl$_2$, wash the extract with water, then dry the extract over MgSO$_4$. Filter, evaporate the solvent, then recrystallize the residue from CH$_2$Cl$_2$/hexane to give the title compound, mp 151°–152° C.

Using substantially the same procedure, cis-N-[2-(3',5'-dichloro-4'-hydroxyphenyl)indanyl]-α-phenylbenzeneacetamide (8A), mp 118°–120° C., can be prepared.

EXAMPLE 9

(+)-cis-N-[2-(4'-hydroxy-3'-methylphenyl)indanyl]-α-phenylbenzeneacetamide

Combine the compound of Example 3AA (5.0 g) in 30 mL of 37% aqueous formaldehyde with 25 mL of 10% KOH (aqueous) in 100 mL of DMF and heat the mixture at 65°–70° C. for 2 hours. Add 10 mL of formaldehyde and 10 mL of 10% KOH and continue heating for 2 hours. Pour the mixture into water and extract with EtOAc. Treat the aqueous layer with brine and again extract with EtOAc. Combine the extracts and dry over Na$_2$SO$_4$, then filter and evaporate to a residue. Chromatograph the residue over silica gel (using 1:1 hexane/EtOAc) to give 0.45 g of monohydroxymethylated product and 0.48 g of bishydroxymethylated product.

Dissolve the monohydroxymethylated product (1.0 g) in 25 mL of HOAc containing 0.4 g of 20% Pd(OH)$_2$ on carbon. Hydrogenate under 60 PSI hydrogen for 24 hours. Chromatograph the product over silica gel (using 2:1 hexane/EtOAc) to give 0.313 g of the title compound, mp 150°–151.5° C.

Hydrogenation using substantially the same procedure but starting with the bishydroxymethylated product gives (+)-cis-N-[2-(3',5'-dimethyl-4'-hydroxyphenyl)indanyl]-α-phenylbenzeneacetamide (9A), mp 162°–164° C.

Using the assay methods described above, the compounds of Examples 1–9 were tested for in vitro ACAT inhibitory activity and for the ability to lower the level of cholesteryl esters in vivo. The results of these tests are as follows:

| Example # | ACAT % Inhibition dose = 10 µM | % Reduction in cholesteryl esters (dose in mpk) |
|---|---|---|
| 1 | −13 | 0 (50) |
| 1A | 54.5 | — |
| 1B | 53 | 21 (50) |
| 1C | 88.5 | — |
| 1D | 75 | 0 (50) |
| 1E | 40 | 0 (50) |
| 1F | 36 | 0 (50) |
| 1G | 51 | 0 (50) |
| 1H | 84 | 0 (50) |
| 1I | 63 | — |
| 1J | 94 | −39 (50) |
| 1K | 43.6 | — |
| 1L | 3 | — |
| 1M | 85 | 0 (50) |
| 1N | 25 | — |

-continued

| Example # | ACAT % Inhibition dose = 10 μM | % Reduction in cholesteryl esters (dose in mpk) |
|---|---|---|
| 1O | 28 | — |
| 1P | 12 | — |
| 1Q | 41 | — |
| 1R | 65 | 0 (50) |
| 1S | — | — |
| 2 | 96 | −17 (50) |
| 2A | 99 | 0 (50) |
| 2B | 94 | — |
| 2C | 99 | 0 (50) |
| 2D | 90 | — |
| 2E | — | — |
| 2F | 19 | 0 (50) |
| 2G | 73 | 0 (100) |
| 2H | 81 | 0 (100) |
| 2I | 51 | — |
| 2J | −12 | — |
| 2K | 90 | 17 (25) |
| 2L | 66 | — |
| 2M | 99 | 0 (100) |
| 2N | 85 | 0 (100) |
| 2O | 87 | — |
| 2P | 97 | −57 (50) −46 (50) −15 (25) |
| 2Q | 16 | — |
| 2R | 75 | 0 (50) |
| 2S | 83 | 16 (50) |
| 2T | 15 | — |
| 3 | 99 | −89 (50) −87.5 (25) −71 (10) |
| 3A | 83 | 0 (50) |
| 3B | 97 | 0 (50) |
| 3C | 77 | 0 (50) |
| 3D | 98 | 0 (50) |
| 3E | 99 | −52 (50) |
| 3F | 91 | −16 (50) |
| 3G | 93 | −57 (50) −43 (25) |
| 3H | 86 | 0 (50) |
| 3I | 99 | −16 (50) |
| 3J | 96 | −61 (50) |
| 3K | 54 | 0 (50) |
| 3L | 93 | — |
| 3M | 87 | −45 (50) |
| 3N | 92 | 0 (50) |
| 3O | 75 | — |
| 3P | 75 | 0 (50) |
| 3Q | 94 | −78 (50) |
| 3R | 75 | 0 (50) |
| 3S | 61 | 0 (50) |
| 3T | 80 | 0 (50) |
| 3U | 98 | −97 (50) −86 (30) −60 (10) |
| 3V | 88 | 0 (50) |
| 3W | 84 | 14 (50) |
| 3X | 97 | — |
| 3Y | 83 | — |
| 3Z | 92 | — |
| 3AA | — | −88 (5) −73 (1) −56 (1) |
| 3BB | <0 | 0 (5) 0 (1) |
| 3CC | 68 | −20 (50) |
| 4 | 94 | 0 (50) |
| 4A | 81 | 0 (50) |
| 5 | 94 | — |
| 5A | 95 | 0 (10) |
| 6 | 97 | −16 (50) |
| 7 | 100 | −40 (50) |
| 8 | 99 | −40 (50) |
| 8A | 99 | −14 (50) |
| 9 | 98 | −66 (50) |
| 9A | 97 | −60 (50) |

The following formulations exemplify some of the dosage forms of this invention. In each the term "active compound" designates a compound of formula I, preferably N-[2-(4'-hydroxyphenyl)indanyl]-α-phenylbenzeneacetamide. However, this compound may be replaced by an equally effective amount of other compounds of formula I.

EXAMPLE A
Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|  | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B
Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|  | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

We claim:

1. A compound represented by the formula

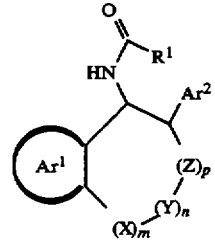

wherein:

Ar¹ is phenyl or R²-substituted phenyl;
Ar² is phenyl, R²-substituted phenyl or pyridyl;
R² is 1 to 3 substituents independently selected from the group consisting of halogeno, hydroxy, lower alkyl, lower alkoxy, nitro, amino, lower alkylamino and lower dialkylamino;
X, Y and Z are independently selected from the group consisting of —CH₂—, —CH(alkyl)— and —C(alkyl)₂—, wherein m, n and p are 0 or 1, such that 0<(m+n+p)<4;

R¹ is a saturated alkyl chain, branched or straight, of 6 to 25 carbon atoms; an unsaturated alkyl chain, branched or straight, of 2 to 25 carbon atoms; a saturated alkyl chain, branched or straight, of 1 to 25 carbon atoms substituted by 1 to 4 substituents selected from the group consisting of phenyl and R²-substituted phenyl; a saturated alkyl chain, branched or straight, of 3 to 25 carbon atoms interrupted by 1 to 4 Q groups, wherein Q is independently selected from the group consisting of —O—, phenylene and R²-substituted phenylene; a saturated alkyl chain of 6 to 25 carbon atoms, interrupted by 1 to 4 groups selected from the group consisting of Q and —C(O)—, and substituted by 1 to 4 substituents selected from the group consisting of phenyl and R²-substituted phenyl; a diphenylamino group; or a di-(R²-substituted phenyl)amino group;

or a pharmaceutically acceptable salt thereof.

2. A compound of claim 1 wherein —(X)$_m$—(Y)$_n$—(Z)$_p$—, together with the carbons to which they are attached, form a 6-C ring.

3. A compound of claim 1 wherein —(X)$_m$—(Y)$_n$—(Z)$_p$—, together with the carbons to which they are attached, form a 7-C ring.

4. A compound of claim 1 wherein —(X)$_m$—(Y)$_n$—(Z)$_p$—, together with the carbons to which they are attached, form a 5-C ring.

5. A compound of claim 1 wherein Ar¹ and Ar² are independently selected from the group consisting of phenyl, nitro-substituted phenyl, amino-substituted phenyl, lower alkoxy-substituted phenyl, hydroxy-substituted phenyl and pyridyl.

6. A compound of claim 1 wherein —C(O)—R¹— is selected from the group consisting of oleoyl, stearoyl, palmitoyl, linoleoyl, linolenoyl, elaidoyl, arachidonoyl, eicosapentaenoyl, eicosatetraenoyl, phenylacetyl, diphenylacetyl, 3,3-diphenylpropionyl, 2,2-dimethylundecanoyl, 2,3-diphenylpropionyl, 3-methoxy-4-(tetradecyloxy)benzoyl, phenoxyundecanoyl and N,N-diphenylaminocarbonyl.

7. A compound of claim 6 wherein —C(O)—R¹— is diphenylacetyl, 2,2-dimethylundecanoyl, oleoyl or N,N-diphenylaminocarbonyl.

8. A compound of claim 1 selected from the group of compounds represented by the formula:

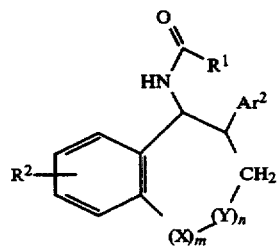

wherein R², Ar², —C(O)R¹, X, Y, m, n, and cis and trans isomers are as defined in the following table:

| cis or trans | R² | Ar² | —CR¹ (C=O) | X | Y | m | n |
|---|---|---|---|---|---|---|---|
| cis | H | 2-methoxyphenyl | diphenylacetyl | — | CH₂ | 0 | 1 |
| trans | H | 2-methoxyphenyl | diphenylacetyl | — | CH₂ | 0 | 1 |
| cis | H | 3-methoxyphenyl | diphenylacetyl | — | CH₂ | 0 | 1 |
| trans | H | 3-methoxyphenyl | diphenylacetyl | — | CH₂ | 0 | 1 |
| trans | H | 4-methoxyphenyl | 2,2-dimethylundecanoyl | — | CH₂ | 0 | 1 |
| trans | H | 4-methoxyphenyl | diphenylacetyl | — | CH₂ | 0 | 1 |
| cis | H | 4-methoxyphenyl | diphenylacetyl | CH₂ | CH₂ | 1 | 1 |
| trans | H | 4-methoxyphenyl | diphenylacetyl | CH₂ | CH₂ | 1 | 1 |
| trans | H | pyridyl | diphenylacetyl | — | CH₂ | 0 | 1 |
| cis | 6-MeO— | C₆H₅ | diphenylacetyl | — | CH₂ | 0 | 1 |
| cis | 7-MeO— | C₆H₅ | diphenylacetyl | — | CH₂ | 0 | 1 |
| trans | 7-MeO— | C₆H₅ | diphenylacetyl | — | CH₂ | 0 | 1 |
| cis | 5-MeO— | C₆H₅ | diphenylacetyl | — | CH₂ | 0 | 1 |
| trans | 5-MeO— | C₆H₅ | diphenylacetyl | — | CH₂ | 0 | 1 |
| trans | 7-MeO— | 4-methoxyphenyl | diphenylacetyl | — | CH₂ | 0 | 1 |
| cis | 7-MeO— | 4-methoxyphenyl | diphenylacetyl | — | CH₂ | 0 | 1 |
| cis | H | 3-methoxyphenyl | diphenylacetyl | — | — | 0 | 0 |
| trans | H | 3-methoxyphenyl | diphenylacetyl | — | — | 0 | 0 |
| cis | H | 3-nitrophenyl | diphenylacetyl | — | — | 0 | 0 |
| trans | H | 3-nitrophenyl | diphenylacetyl | — | — | 0 | 0 |
| cis | 7-OH | C₆H₅ | diphenylacetyl | — | — | 0 | 0 |
| trans | H | 4-methoxyphenyl | diphenylacetyl | — | — | 0 | 0 |
| cis | H | 4-methoxyphenyl | oleoyl | — | CH₂ | 0 | 1 |
| trans | H | 4-methoxyphenyl | oleoyl | — | CH₂ | 0 | 1 |
| cis | H | 4-nitrophenyl | diphenylacetyl | — | — | 0 | 0 |
| cis | H | 4-methoxyphenyl | diphenylacetyl | — | — | 0 | 0 |
| trans | 5-MeO— | C₆H₅ | diphenylacetyl | — | — | 0 | 0 |
| cis | H | C₆H₅ | oleoyl | — | CH₂ | 0 | 1 |
| trans | H | C₆H₅ | oleoyl | — | CH₂ | 0 | 1 |
| trans | H | 4-aminophenyl | diphenylacetyl | — | CH₂ | 0 | 1 |
| cis | 6-MeO— | C₆H₅ | diphenylacetyl | — | — | 0 | 0 |
| cis | 5-MeO— | C₆H₅ | diphenylacetyl | — | — | 0 | 0 |
| trans | H | 2-hydroxyphenyl | diphenylacetyl | — | CH₂ | 0 | 1 |
| cis | H | 3-hydroxyphenyl | diphenylacetyl | — | — | 0 | 0 |
| cis | H | 3-hydroxyphenyl | diphenylacetyl | — | CH₂ | 0 | 1 |
| trans | H | 3-hydroxyphenyl | diphenylacetyl | — | CH₂ | 0 | 1 |
| cis | H | 4-hydroxyphenyl | diphenylacetyl | — | — | 0 | 0 |
| trans | H | 4-hydroxyphenyl | diphenylacetyl | — | — | 0 | 0 |
| cis | H | 4-hydroxyphenyl | diphenylacetyl | — | CH₂ | 0 | 1 |
| trans | H | 4-hydroxyphenyl | diphenylacetyl | — | CH₂ | 0 | 1 |
| trans | H | 4-hydroxyphenyl | 2,2-dimethyl- | — | CH₂ | 0 | 1 |

-continued

| cis or trans | R² | Ar² | —CR¹ (C=O) | X | Y | m | n |
|---|---|---|---|---|---|---|---|
| | | | undecanoyl | | | | |
| trans | H | 4-hydroxyphenyl | —CN(Ph)₂ (C=O) | — | CH₂ | 0 | 1 |
| trans | H | 4-hydroxyphenyl | diphenylacetyl | CH₂ | CH₂ | 1 | 1 |
| cis | 5-OH | C₆H₅ | diphenylacetyl | — | — | 0 | 0 |
| trans | 5-OH | C₆H₅ | diphenylacetyl | — | — | 0 | 0 |
| cis | 6-OH | C₆H₅ | diphenylacetyl | — | CH₂ | 0 | 1 |
| trans | 6-OH | C₆H₅ | diphenylacetyl | — | CH₂ | 0 | 1 |
| cis | H | 2-hydroxyphenyl | diphenylacetyl | — | CH₂ | 0 | 1 |
| cis | 7-OH | C₆H₅ | diphenylacetyl | — | CH₂ | 0 | 1 |
| trans | 7-OH | C₆H₅ | diphenylacetyl | — | CH₂ | 0 | 1 |
| cis | H | 4-hydroxyphenyl | diphenylacetyl | CH₂ | CH₂ | 1 | 1 |
| trans | 5-OH | C₆H₅ | diphenylacetyl | — | CH₂ | 0 | 1 |
| cis | 5-OH | C₆H₅ | diphenylacetyl | — | CH₂ | 0 | 1 |
| trans | 7-OH | 4-hydroxyphenyl | diphenylacetyl | — | CH₂ | 0 | 1 |
| cis | 7-OH | 4-hydroxyphenyl | diphenylacetyl | — | CH₂ | 0 | 1 |
| cis | 6-OH | C₆H₅ | diphenylacetyl | — | — | 0 | 0 |
| cis | 7-OH | C₆H₅ | diphenylacetyl | — | — | 0 | 0 |
| (+)-trans | 7-OH | C₆H₅ | diphenylacetyl | — | CH₂ | 0 | 1 |
| (−)-trans | 7-OH | C₆H₅ | diphenylacetyl | — | CH₂ | 0 | 1 |
| (+)-cis | H | 4-hydroxyphenyl | diphenylacetyl | — | — | 0 | 0 |
| trans | 8-OH | C₆H₅ | diphenylacetyl | — | CH₂ | 0 | 1 |
| cis | H | 4-hydroxyphenyl | oleoyl | — | CH₂ | 0 | 1 |
| trans | H | 4-hydroxyphenyl | oleoyl | — | CH₂ | 0 | 1 |
| cis | H | 3-aminophenyl | diphenylacetyl | — | — | 0 | 0 |
| trans | H | 4-aminophenyl | diphenylacetyl | — | — | 0 | 0 |
| trans | H | 4-methoxyphenyl | —CN(Ph)₂ (C=O) | — | CH₂ | 0 | 1 |
| (+)-cis | H | 3-Br-4-OH-phenyl | diphenylacetyl | — | — | 0 | 0 |
| cis | H | 3-Cl-4-OH-phenyl | diphenylacetyl | — | — | 0 | 0 |
| cis | H | 3,5-di-Cl-4-OH-phenyl | diphenylacetyl | — | — | 0 | 0 |
| (+)-cis | H | 4-hydroxy-3-methylphenyl | diphenylacetyl | — | — | 0 | 0 |
| (+)-cis | H | 3,5-di-methyl-4-hydroxyphenyl | diphenylacetyl | — | — | 0 | 0 |

9. A compound of claim 1 having the chemical structure

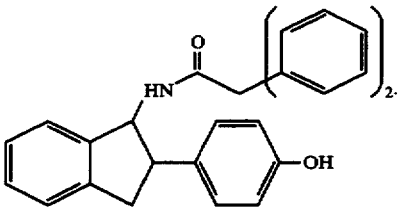

10. A pharmaceutical composition for treating atherosclerosis comprising an ACAT-inhibitory effective amount of a compound of claim 1 in a pharmaceutically effective carrier.

11. A method of treating atherosclerosis comprising administering to a mammal in need of such treatment a pharmaceutical composition of claim 10.

12. A method of treating atherosclerosis comprising administering to a mammal in need of such treatment an effective amount of a compound of claim 1.

* * * * *